(12) United States Patent
Jeffery

(10) Patent No.: US 10,258,788 B2
(45) Date of Patent: Apr. 16, 2019

(54) ELECTRODES HAVING SURFACE EXCLUSIONS

(71) Applicant: Thync Global, Inc., Los Gatos, CA (US)

(72) Inventor: Douglas Jeffery, San Jose, CA (US)

(73) Assignee: Thync Global, Inc., Los Gatos, CA (US)

( * ) Notice: Subject to any disclaimer, the term of this patent is extended or adjusted under 35 U.S.C. 154(b) by 0 days.

(21) Appl. No.: 15/380,028

(22) Filed: Dec. 15, 2016

(65) Prior Publication Data

US 2017/0165470 A1 Jun. 15, 2017

Related U.S. Application Data

(60) Provisional application No. 62/267,290, filed on Dec. 15, 2015.

(51) Int. Cl.
*A61N 1/00* (2006.01)
*A61N 1/04* (2006.01)
*A61N 1/36* (2006.01)

(52) U.S. Cl.
CPC .......... *A61N 1/0496* (2013.01); *A61N 1/048* (2013.01); *A61N 1/0456* (2013.01); *A61N 1/36014* (2013.01); *A61N 1/0476* (2013.01)

(58) Field of Classification Search
CPC .. A61N 1/0492; A61N 1/0456; A61N 1/0496; A61N 1/048; A61N 1/36014; A61N 1/0476; A61N 1/36025
See application file for complete search history.

(56) References Cited

U.S. PATENT DOCUMENTS

| | | | |
|---|---|---|---|
| 3,255,753 | A | 6/1966 | Wing |
| 3,388,699 | A | 6/1968 | Webb et al. |
| 3,620,219 | A | 11/1971 | Barker |

(Continued)

FOREIGN PATENT DOCUMENTS

| | | |
|---|---|---|
| CN | 1204268 A | 1/1999 |
| CN | 1607970 A | 4/2005 |

(Continued)

OTHER PUBLICATIONS

Pal et al.; U.S. Appl. No. 14/956,193 entitled "Transdermal electrical stimulation devices for modifying or inducing cognitive state," filed Dec. 1, 2015.

(Continued)

*Primary Examiner* — Mallika D Fairchild
(74) *Attorney, Agent, or Firm* — Shay Glenn LLP

(57) ABSTRACT

Electrodes having an active region formed of a plurality of layers in which one or more conductive layers is formed of a pattern having a plurality of branches and/or holes (e.g. a grid pattern, a snowflake pattern, etc.) to provide a greater density of edges, so that the ratio of edges in the patterned conductive layer to the perimeter of the active region is greater than a minimum value (e.g., 1.5, 2, 3, 4, 5, 6, etc.). The multiple layers may include the patterned conductive layer and a second conductive layer, which may also be patterned, with a less conductive layer sandwiched between them to achieve a more even charge distribution across the face of the active region than in addition to the greater current density provided by the large number of edges.

19 Claims, 20 Drawing Sheets

(56) References Cited

U.S. PATENT DOCUMENTS

| | | |
|---|---|---|
| 3,648,708 A | 3/1972 | Haeri |
| 3,762,396 A | 10/1973 | Ballentine et al. |
| 4,418,687 A | 12/1983 | Matsumoto et al. |
| 4,431,000 A | 2/1984 | Butler et al. |
| 4,646,744 A | 3/1987 | Capel |
| 4,664,117 A | 5/1987 | Beck |
| 4,865,048 A | 9/1989 | Eckerson |
| 5,144,952 A | 9/1992 | Frachet et al. |
| 5,183,041 A | 2/1993 | Toriu et al. |
| 5,335,657 A | 8/1994 | Terry et al. |
| 5,342,410 A | 8/1994 | Braverman |
| 5,397,338 A | 3/1995 | Grey et al. |
| 5,476,481 A | 12/1995 | Schondorf |
| 5,487,759 A | 1/1996 | Bastyr et al. |
| 5,514,175 A | 5/1996 | Kim et al. |
| 5,540,736 A | 7/1996 | Haimovich et al. |
| 5,573,552 A | 11/1996 | Hansjurgens |
| 5,578,065 A | 11/1996 | Hattori et al. |
| 5,593,427 A | 1/1997 | Gliner et al. |
| 5,738,647 A | 4/1998 | Bernhard et al. |
| 5,792,067 A | 8/1998 | Karell |
| 6,066,163 A | 5/2000 | John |
| 6,280,454 B1 | 8/2001 | Wang |
| 6,324,432 B1 | 11/2001 | Rigaux et al. |
| 6,445,955 B1 | 9/2002 | Michelson et al. |
| 6,463,328 B1 | 10/2002 | John |
| 6,516,227 B1 | 2/2003 | Meadows et al. |
| 6,526,318 B1 | 2/2003 | Ansarinia |
| 6,567,702 B1 | 5/2003 | Nekhendzy et al. |
| 6,731,987 B1 | 5/2004 | McAdams et al. |
| 6,983,184 B2 | 1/2006 | Price |
| 7,120,499 B2 | 10/2006 | Thrope et al. |
| 7,146,217 B2 | 12/2006 | Firlik et al. |
| 7,263,501 B2 | 8/2007 | Tirinato et al. |
| 7,376,467 B2 | 5/2008 | Thrope et al. |
| 7,422,555 B2 | 9/2008 | Zabara |
| 7,577,481 B2 | 8/2009 | Firlik et al. |
| 7,660,636 B2 | 2/2010 | Castel et al. |
| 7,801,600 B1 | 9/2010 | Carbunaru et al. |
| 7,891,615 B2 | 2/2011 | Bevirt |
| 7,949,403 B2 | 5/2011 | Palermo et al. |
| 8,029,431 B2 | 10/2011 | Tononi |
| 8,034,294 B1 | 10/2011 | Goldberg |
| 8,086,318 B2 | 12/2011 | Strother et al. |
| 8,097,926 B2 | 1/2012 | De Graff et al. |
| 8,116,875 B2 | 2/2012 | Osypka et al. |
| 8,121,695 B2 | 2/2012 | Gliner et al. |
| 8,150,537 B2 | 4/2012 | Tanaka et al. |
| 8,190,248 B2 | 5/2012 | Besio et al. |
| 8,197,276 B2 | 6/2012 | Egloff et al. |
| 8,204,601 B2 | 6/2012 | Moyer et al. |
| 8,239,030 B1 | 8/2012 | Hagedorn et al. |
| 8,265,761 B2 | 9/2012 | Siever |
| 8,280,502 B2 | 10/2012 | Hargrove et al. |
| 346,337 A1 | 1/2013 | Heller et al. |
| 8,380,315 B2 | 2/2013 | DeGiorgio et al. |
| 8,428,738 B2 | 4/2013 | Valencia |
| 8,463,383 B2 | 6/2013 | Sakai et al. |
| 8,494,625 B2 | 7/2013 | Hargrove |
| 8,494,627 B2 | 7/2013 | Bikson et al. |
| 8,506,469 B2 | 8/2013 | Dietrich et al. |
| 8,532,758 B2 | 9/2013 | Silverstone |
| 8,560,075 B2 | 10/2013 | Covalin |
| 8,571,651 B2 | 10/2013 | Ben-Ezra et al. |
| 8,583,238 B1 | 11/2013 | Heldman et al. |
| 8,583,256 B2 | 11/2013 | Tracey et al. |
| 8,612,005 B2 | 12/2013 | Rezai et al. |
| 8,639,343 B2 | 1/2014 | De Vos |
| 8,660,644 B2 | 2/2014 | Jaax et al. |
| 8,688,239 B2 | 4/2014 | Hartlep et al. |
| 8,843,210 B2 | 9/2014 | Simon et al. |
| 8,874,219 B2 | 10/2014 | Trier et al. |
| 8,903,494 B2 | 12/2014 | Goldwasser et al. |
| 8,983,621 B2 | 3/2015 | Hou et al. |
| 9,002,458 B2 | 4/2015 | Pal et al. |
| 9,014,811 B2 | 4/2015 | Pal et al. |
| 9,067,054 B2 | 6/2015 | Simon et al. |
| 9,168,374 B2 | 10/2015 | Su |
| 9,205,258 B2 | 12/2015 | Simon et al. |
| 9,233,244 B2 | 1/2016 | Pal et al. |
| 9,248,292 B2 | 2/2016 | Trier et al. |
| 9,333,334 B2 | 5/2016 | Jeffery et al. |
| 9,364,674 B2 | 6/2016 | Cook et al. |
| 9,393,401 B2 | 7/2016 | Goldwasser et al. |
| 9,393,430 B2 | 7/2016 | Demers et al. |
| 9,399,126 B2 | 7/2016 | Pal et al. |
| 9,415,219 B2 | 8/2016 | Simon et al. |
| 9,440,070 B2 | 9/2016 | Goldwasser et al. |
| 9,446,242 B2 | 9/2016 | Griffith |
| 9,474,891 B2 | 10/2016 | Demers et al. |
| 9,474,905 B2 | 10/2016 | Doan et al. |
| 9,517,351 B2 | 12/2016 | Charlesworth et al. |
| 9,656,076 B2 | 5/2017 | Trier et al. |
| 9,700,725 B2 | 7/2017 | Zhu |
| 9,731,116 B2 | 8/2017 | Chen |
| 9,744,347 B2 | 8/2017 | Chen et al. |
| 9,764,133 B2 | 9/2017 | Thomas et al. |
| 9,782,587 B2 | 10/2017 | Trier et al. |
| 2001/0000187 A1 | 4/2001 | Peckham et al. |
| 2002/0116036 A1 | 8/2002 | Daignault et al. |
| 2003/0088279 A1 | 5/2003 | Rissmann et al. |
| 2003/0134545 A1 | 7/2003 | McAdams et al. |
| 2003/0171685 A1 | 9/2003 | Lesser et al. |
| 2003/0225323 A1 | 12/2003 | Kiani et al. |
| 2004/0019370 A1 | 1/2004 | Gliner et al. |
| 2004/0098065 A1 | 5/2004 | Hagglof et al. |
| 2004/0158305 A1 | 8/2004 | Axelgaard |
| 2004/0267333 A1 | 12/2004 | Kronberg |
| 2005/0165460 A1 | 7/2005 | Erfan |
| 2005/0267388 A1 | 12/2005 | Hanna |
| 2005/0283259 A1 | 12/2005 | Wolpow |
| 2006/0064139 A1 | 3/2006 | Chung et al. |
| 2006/0149119 A1 | 7/2006 | Wang |
| 2006/0190057 A1 | 8/2006 | Reese |
| 2006/0195159 A1 | 8/2006 | Bradley et al. |
| 2006/0206163 A1 | 9/2006 | Wahlstrand et al. |
| 2006/0247985 A1 | 11/2006 | Liamos et al. |
| 2007/0053466 A1 | 3/2007 | Klostermann |
| 2007/0088419 A1 | 4/2007 | Fiorina et al. |
| 2007/0097593 A1 | 5/2007 | Armstrong |
| 2007/0100275 A1 | 5/2007 | Fischer et al. |
| 2007/0173890 A1 | 7/2007 | Armstrong |
| 2007/0213790 A1 | 9/2007 | Nolan et al. |
| 2007/0276451 A1 | 11/2007 | Rigaux |
| 2008/0015641 A1 | 1/2008 | Armstrong et al. |
| 2008/0045882 A1 | 2/2008 | Finsterwald |
| 2008/0071626 A1 | 3/2008 | Hill |
| 2008/0132974 A1 | 6/2008 | Strother et al. |
| 2008/0207985 A1 | 8/2008 | Farone |
| 2008/0208266 A1 | 8/2008 | Lesser et al. |
| 2008/0215113 A1 | 9/2008 | Pawlowicz |
| 2008/0275293 A1 | 11/2008 | Lattner et al. |
| 2008/0281368 A1 | 11/2008 | Bulkes et al. |
| 2008/0319505 A1 | 12/2008 | Boyden et al. |
| 2009/0048642 A1 | 2/2009 | Goroszeniuk |
| 2009/0054952 A1 | 2/2009 | Glukhovsky et al. |
| 2009/0099623 A1 | 4/2009 | Bentwich |
| 2009/0112280 A1 | 4/2009 | Wingeier et al. |
| 2009/0177243 A1 | 7/2009 | Lebedev et al. |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0057154 A1 | 3/2010 | Dietrich et al. |
| 2010/0076533 A1 | 3/2010 | Dar et al. |
| 2010/0094375 A1 | 4/2010 | Donders et al. |
| 2010/0145399 A1 | 6/2010 | Johari et al. |
| 2010/0152817 A1 | 6/2010 | Gillbe |
| 2010/0256436 A1 | 10/2010 | Partsch et al. |
| 2010/0318168 A1 | 12/2010 | Bignetti |
| 2011/0029045 A1 | 2/2011 | Cevette et al. |
| 2011/0034756 A1 | 2/2011 | Hacking et al. |
| 2011/0077660 A1 | 3/2011 | Janik et al. |
| 2011/0082326 A1 | 4/2011 | Mishelevich et al. |

(56) References Cited

U.S. PATENT DOCUMENTS

| | | |
|---|---|---|
| 2011/0082515 A1 | 4/2011 | Libbus et al. |
| 2011/0093033 A1 | 4/2011 | Nekhendzy |
| 2011/0112394 A1 | 5/2011 | Mishelevich |
| 2011/0112590 A1 | 5/2011 | Wu et al. |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0172752 A1 | 7/2011 | Bingham et al. |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |
| 2011/0276112 A1 | 11/2011 | Simon et al. |
| 2011/0288610 A1 | 11/2011 | Brooke |
| 2011/0301683 A1* | 12/2011 | Axelgaard ........... A61N 1/0452 607/149 |
| 2011/0307029 A1 | 12/2011 | Hargrove |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0182924 A1 | 7/2012 | Gaines et al. |
| 2012/0184801 A1 | 7/2012 | Simon et al. |
| 2012/0185020 A1 | 7/2012 | Simon et al. |
| 2012/0209340 A1 | 8/2012 | Escribano |
| 2012/0209346 A1 | 8/2012 | Bikson et al. |
| 2012/0245409 A1 | 9/2012 | Liang |
| 2012/0245653 A1 | 9/2012 | Bikson et al. |
| 2012/0296390 A1 | 11/2012 | Nakashima et al. |
| 2012/0302912 A1 | 11/2012 | Moffitt et al. |
| 2012/0306628 A1 | 12/2012 | Singhal |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0096641 A1 | 4/2013 | Strother et al. |
| 2013/0131551 A1 | 5/2013 | Raghunathan et al. |
| 2013/0158627 A1 | 6/2013 | Gozani et al. |
| 2013/0184779 A1 | 7/2013 | Bikson et al. |
| 2013/0204315 A1 | 8/2013 | Wongsarnpigoon et al. |
| 2013/0226275 A1 | 8/2013 | Duncan |
| 2013/0253613 A1 | 9/2013 | Salahovic et al. |
| 2013/0267761 A1 | 10/2013 | Bentwich |
| 2013/0282095 A1 | 10/2013 | Mignolet et al. |
| 2013/0304175 A1 | 11/2013 | Voegele et al. |
| 2013/0318168 A1 | 11/2013 | Demain et al. |
| 2013/0325096 A1 | 12/2013 | Dupelle |
| 2014/0031895 A1 | 1/2014 | Rahimi et al. |
| 2014/0128939 A1 | 5/2014 | Embrey et al. |
| 2014/0128944 A1 | 5/2014 | Stern et al. |
| 2014/0163645 A1 | 6/2014 | Dinsmoor et al. |
| 2014/0182350 A1 | 7/2014 | Bhavaraju et al. |
| 2014/0222102 A1 | 8/2014 | Lemus et al. |
| 2014/0257449 A1 | 9/2014 | Helmer |
| 2014/0275933 A1* | 9/2014 | Meyer .................. A61B 5/0416 600/391 |
| 2014/0277324 A1 | 9/2014 | DiUbaldi et al. |
| 2014/0309709 A1 | 10/2014 | Gozani et al. |
| 2014/0336728 A1 | 11/2014 | Franke et al. |
| 2014/0371814 A1 | 12/2014 | Spizzirri et al. |
| 2015/0066104 A1 | 3/2015 | Wingeier et al. |
| 2015/0224310 A1 | 8/2015 | Sharma et al. |
| 2015/0230863 A1 | 8/2015 | Youngquist et al. |
| 2015/0257970 A1 | 9/2015 | Mucke et al. |
| 2015/0335877 A1* | 11/2015 | Jeffery ................. A61N 1/0492 607/139 |
| 2016/0008632 A1 | 1/2016 | Wetmore et al. |
| 2016/0074657 A1 | 3/2016 | Kwan et al. |
| 2016/0279435 A1 | 9/2016 | Hyde et al. |
| 2016/0317809 A1 | 11/2016 | Pal et al. |
| 2016/0346530 A1 | 12/2016 | Jeffery et al. |
| 2016/0346545 A1 | 12/2016 | Pal et al. |

FOREIGN PATENT DOCUMENTS

| | | |
|---|---|---|
| CN | 1704131 A | 12/2005 |
| CN | 1842356 A | 10/2006 |
| CN | 101234233 A | 8/2008 |
| CN | 101244314 A | 8/2008 |
| CN | 201353374 Y | 12/2009 |
| CN | 102245253 A | 11/2011 |
| CN | 102725021 A | 10/2012 |
| CN | 102906752 A | 1/2013 |
| CN | 103517732 A | 1/2014 |
| EP | 502919 B1 | 11/1993 |
| EP | 801957 A1 | 10/1997 |
| EP | 09965358 A2 | 12/1999 |
| EP | 1529550 A1 | 5/2005 |
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49061984 A | 6/1974 |
| JP | 05031197 A | 2/1993 |
| JP | 10108913 A | 4/1998 |
| JP | 2001129100 A | 5/2001 |
| JP | 2001293097 A | 10/2001 |
| JP | 2002-306604 A | 10/2002 |
| JP | 200310230 A | 1/2003 |
| JP | 2006192302 A | 7/2006 |
| JP | 3129187 U | 1/2007 |
| JP | 200985901 A | 4/2009 |
| JP | 2011118293 A | 6/2011 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/08071 A1 | 2/2001 |
| WO | WO01/78834 A1 | 10/2001 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2010/120823 A2 | 10/2010 |
| WO | WO2011/044176 A1 | 4/2011 |
| WO | WO2011/147546 A1 | 12/2011 |
| WO | WO2012/082960 A2 | 6/2012 |
| WO | WO2012/089588 A1 | 7/2012 |
| WO | WO2012/116407 A1 | 9/2012 |
| WO | WO2012/129574 A2 | 9/2012 |
| WO | WO2012/150600 A2 | 11/2012 |
| WO | WO2012/156051 A1 | 11/2012 |
| WO | WO2012/156052 A2 | 11/2012 |
| WO | WO2013/071307 A1 | 5/2013 |
| WO | WO2013/192582 A1 | 12/2013 |
| WO | WO2014/107624 A1 | 7/2014 |
| WO | WO2014/195516 A1 | 12/2014 |
| WO | WO2015/036420 A1 | 3/2015 |
| WO | WO2015/061663 A1 | 4/2015 |
| WO | WO2015/143053 A1 | 9/2015 |
| WO | WO2015/183690 A1 | 12/2015 |

OTHER PUBLICATIONS

Tyler et al.; U.S. Appl. No. 15/536,148 entitled "Methods and apparatuses for transdermal stimulation of the outer ear," filed Jun. 15, 2017.

(56) References Cited

OTHER PUBLICATIONS

Tyler et al.; U.S. Appl. No. 15/536,151 entitled "Systems and methods for transdermal electrical stimulation to improve sleep," filed Jun. 15, 2017.
Axelgaard Manufacturing Co. Ltd.; Little PALS® (product information); 2 pgs.; printed Feb. 11, 2013 from http://www.axelgaard.com/prod_little-pals.html.
Axelgaard Manufacturing Co. Ltd.; PALS® Platinum Blue (product information); 2 pgs.; printed Feb. 11, 2013 from http://www.axelgaard.com/prod_pals-platinum-blue.html.
Chaieb et al.; Transcranial alternating current stimulation in the low kHz range increases motor cortex excitability; Restor Neurol Neurosci; 29(3); pp. 167-175; Mar. 2011.
Coutinho et al.; Musical emotions: predicting second-by-second subjective feelings of emotion from low-level psychoacoustic features and physiological measurements; Emotion; 11(4); pp. 921-937; Aug. 2011.
DaSilva et al.; Electrode positioning and montage in transcranial direct current stimulation; J Vis Exp; 51; e2744; 11 pgs.; May 2011.
Digitimer Ltd.; DS2 and DS3 Isolated Stimulator (product information); 2 pgs.; downloaded from http://www.digitimer.com/research/stimulators/index.htm on Feb. 10, 2014.
Electozyme; Company and Product Information; 3 pgs.; printed Feb. 11, 2014 from http://electrozyme.com/applications/.
Feurra et al.; Frequency specific modulation of human somatosensory cortex; Front Psychol; 2(13); 6 pgs.; Feb. 2011.
GoFLOW; tDCS Kit; product information; 9 pgs..; printed Feb. 10, 2014 (http://flowstateengaged.com/).
Golestanirad et al; Analysis of fractal electrodes for efficient neural stimulation; Frontiers in Neurengineering; 6(3); 10 pages; Jul. 2013.
Gracenote; Timeline—metadata—api; 3 pages; retrieved from the internet Jul. 7, 2015; (https://github.com/gracenote/timeline-metadata-api/blob/master/README.md).
Grindhouse Wetware; Thinking Cap; product information; 1 pg.; printed Feb. 10, 2014 (http://www.grindhousewetware.com/thinkingcap.html).
Kanai et al.; Frequency-dependent electrical stimulatioin of the visual cortex; Curr. Biol.; 18(23); pp. 1839-1843; Dec. 9, 2008.
Paulus, W.; Transcranial electrical stimulation (tES-tDCS; tRNS, tACS) methods; Neuropsychol Rehabil.; 21(5); pp. 602-617; Oct. 2011.
Prausnitz; The effects of electric current applied to skin: a review for transdermal drug delivery; Advanced Drug Delivery Reviews; vol. 18; pp. 395-425; Feb. 8, 1996.
Saiote et al.; High-frequency TRNS reduces BOLD activity during visuomotor learning; PLOS one; 8(3); e59669; 8 pgs.; Mar. 2013.
Schutter et al.; Brain oscillations and frequency-dependent modulation of cortical excitability; Brain Stimulation; 4(2); pp. 97-103; Apr. 2011.
STD Pharmaceutical Products; Idrostar intophoresis machine (product and use information); 9 pgs.; Dec. 2011 (printed Feb. 11, 2014 from http://www.iontophoresis.info/instructions/).
Terney et al.; Increasing human brain excitability by transcranial high-frequency random noise stimulation; The Journal of Neuroscience; 28(52); pp. 14127-14155; Dec. 2008.
Turi et al.; Both the cutaneous sensation and phosphene perception are modulated in a frequency-specific manner during transcranial alternating current stimulation; Restor. Neurol. Neurosci.; 31(3); pp. 275-285; Jan. 2013.
Tyler et al.; U.S. Appl. No. 61/550,334 entitled "Improvement of Direct Communication," filed Oct. 21, 2011.
Tyler et al.; U.S. Appl. No. 61/663,409 entitled "Device and Methods for Noninvasive Neuromodulation Using Targeted Transcranial Electrical Stimulation," filed Jun. 22, 2012.
Tyler et al.; U.S. Appl. No. 62/166,674 entitled "Systems and Methods for Suppression of Stress Responses by Transdermal Electrical Neuromodulation," filed May 26, 2015.
Goldwasser et al.; U.S. Appl. No. 15/264,224 entitled "Apparatuses and methods for neuromodulation," filed Sep. 13, 2016.
Egnal et al.; U.S. Appl. No. 15/265,633 entitled "Apparatuses and methods for auto-replenishment of electrodes for transdermal electrical stimulation," filed Sep. 14, 2016.
Charlesworth et al.; U.S. Appl. No. 15/384,249 entitled "Apparatuses and methods for transdermal electrical stimulation of nerves to modify or induce a cognitive state," filed Dec. 19, 2017.
Aston-Jones et al.; An integrative theory of locus coeruleus-norepinephrine function: adaptive gain and optimal performance; Annu. Rev. Neurosci.; 28: pp. 403-450; Jul. 21, 2005.
Aston-Jones et al.; Role of locus coeruleus in attention and behavioral flexibility; Biological Psychiatry; 46(9); pp. 1309-1320; Nov. 1, 1999.
Backhaus et al.; Sleep disturbances are correlated with decreased morning awakening salivary cortisol; Psychoneuroendocrinology; 29(9): pp. 1184-1191; Oct. 31, 2004.
Basta et al.; Chronic Insomnia and the Stress System; Sleep Medicine Clinics; 2(2): pp. 279¬291; (Author Manuscript, 20 pages); Jun. 30, 2007.
Berlad et al.; Power spectrum analysis and heart rate variability in Stage 4 and REM sleep: evidence for state-specific changes in autonomic dominance; Journal of Sleep Research; 2(2): pp. 88-90; Jun. 1, 1993.
Berridge et al.; The locus coeruleus-noradrenergic system: modulation of behavioral state and state-dependent cognitive processes; Brain Research Reviews; 42(1); pp. 33-84; Apr. 30, 2003.
Brown et al.; Control of sleep and wakefulness; Physiological reviews; 92(3); pp. 1087-1187; Jul. 1, 2012.
Brown et al.;Locus ceruleus activation suppresses feedforward interneurons and reduces beta-gamma electroencephalogram frequencies while it enhances theta frequencies in rat dentate gyrus; Journals of Neuroscience; 25(8): pp. 1985-1991; Feb. 23, 2005.
Buchanan et al.; Salivary alpha-amylase levels as a biomarker of experienced fear; Communicative and Integrative Biology; 3(6); pp. 525-527; Nov. 1, 2010.
Buckley et al.; On the Interactions of the Hypothalamic-Pituitary-Adrenal (HPA) Axis and Sleep: Normal HPA Axis Activity and Circadian Rhythm, Exemplary Sleep Disorders; The Journal of Clinical Endocrinology and Metabolism; 90 (5); pp. 3106-3114; May 1, 2005.
Buysse et al.; The Pittsburgh Sleep Quality Index: a new instrument for psychiatric practice and research; Psychiatric Research; 28(2); pp. 193-213; May 31, 1989.
Carter et al.; Tuning arousal with optogenetic modulation of locus coeruleus neurons; Nature Neuroscience; 13(12); pp. 1526-1533; Dec. 1, 2010.
Cook et al.; Trigeminal nerve stimulation in major depressive disorder: acute outcomes in an open pilot study; Epilepsy and Behavior; 28(2): pp. 221-226; Aug. 31, 2013.
Degiorgio et al., Trigeminal nerve stimulation for epilepsy: long-term feasibility and efficacy; Neurology; 72(10): pp. 936-938; Mar. 10, 2009.
Degiorgio et al.; Randomized controlled trial of trigeminal nerve stimulation for drug-resistant epilepsy; Neurology; 80(9); pp. 786-791; Feb. 26, 2013.
Elder et al.; The cortisol awakening response—applications and implications for sleep medicine; Sleep Medicine Reviews; 18(3): pp. 215-224; Jun. 30, 2014.
Eschenko et al.; Noradrenergic neurons of the locus coeruleus are phase locked to cortical up-down states during sleep; Cerebral Cortex; 22(2); pp. 426-435; Feb. 1, 2012.
Franowicz et al.; Treatment with the noradrenergic alpha-2 agonist clonidine, but not diazepam, improves spatial working memory in normal young rhesus monkeys; Neuropsychopharmacology; 21(5); pp. 611-621; Nov. 1, 1999.
Garraway et al.; Modulatory actions of serotonin, norepinephrine, dopamine, and acetylcholine in spinal cord deep dorsal horn neurons; Journal of Neurophysiology; 86(5); pp. 2183-2194; Nov. 1, 2001.
Granger et al.; Salivary alpha-amylase in biobehavioral research: recent developments and applications; Annals of the New York Academy of Sciences; 1098(1); pp. 122-144; Mar. 1, 2007.

(56) References Cited

OTHER PUBLICATIONS

Gummadavelli et al.; Neurostimulation to improve level of consciousness in patients with epilepsy. Neurosurgical Focus; 38(6); pp. E10; (manuscript version,14 pages); Jun. 2015.
Hajos et al.; Norepinephrine but not serotonin reuptake inhibitors enhance theta and gamma activity of the septo-hippocampal system; Neuropsychopharmacology; 28(5); pp. 857-864; May 1, 2003.
Hass et al.; Waking with the hypothalamus. Pflugers Arch R Eur. J. Physiol.; 463(1): pp. 31-42; Jan. 1, 2012.
Herwig et al.; Intracortical excitability is modulated by a norepinephrine-reuptake inhibitor as measured with paired-pulse transcranial magnetic stimulation; Psychopharmacology (Berl); 164(2): pp. 228-232; Nov. 18, 2002.
Hirotsu et al.; Interactions between sleep, stress, and metabolism; From physiological to pathological conditions; Sleep Science; 8(3); pp. 143-152; Nov. 2015.
Horvath et al.; Evidence that transcranial direct current stimulation (tDCS) generates little-to-no reliable neurophysiologic effect beyond MEP amplitude modulation in healthy human subjects: A systematic review; Neuropsychologia; 66: pp. 213-236; Jan. 31, 2015.
Just et al.; Bold responses to trigeminal nerve stimulation; Magnetic Resonance Imaging; 28(8): pp. 1143-1151; Oct. 31, 2010.
Kubota et al.; Role of the brain stem in cardiovascular changes induced by stimulation of the trigeminal nerve; Anesthesia Progress; 36(4-5); pp. 236-237; Jul. 1989.
Lee et al.; Neuromodulation of Brain States; Neuron; 76(1): pp. 209-222. Oct. 4, 2012.
Leproult et al.; Sleep loss results in an elevation of cortisol levels the next evening; Sleep; 20(10): pp. 865-870; Oct. 1997.
Lovibond et al.; The structure of negative emotional states: Comparison of the Depression Anxiety Stress Scales (DASS) with the Beck Depression and Anxiety Inventories; Behaviour Research and Therapy; 33(3); pp. 335-343; Mar. 31, 1995.
Lu et al.; A putative flip-flop switch for control of REM sleep; Nature; 441(7093): pp. 589-594; Jun. 1, 2006.
Magis et al.; Safety and patients' satisfaction of transcutaneous supraorbital neurostimulation (tSNS) with the Cefaly(R) device in headache treatment: a survey of 2,313 headache sufferers in the general population; The Journal of Headache and Pain, 14(1); pp. 95; (manuscript version, 8 pages) Dec. 1, 2013.
Mcgough et al.; An eight-week, open-trial, pilot feasibility study of trigeminal nerve stimulation in youth with attention-deficit/hyperactivity disorder; Brain Stimulation; 8(2); pp. 299-304; Apr. 30, 2015.
Meltzer et al; Direct comparison of two new actigraphs and polysomnography in children and adolescents; Sleep; 35(1); pp. 159-166; Jan. 1, 2012.
Nash et al.; Differential activation of the human trigeminal nuclear complex by noxious and non-noxious orofacial stimulation; Human Brain Mapping; 30(11); pp. 3772-3782; Nov. 1, 2009.
Nieuwenhuis et al.; Decision making, the P3, and the locus coeruleus-norepinephrine system; Psychological Bulletin; 131(4); pp. 510-532; Jul. 2005.
Parvizi et al.; Consciousness and the brainstem; Cognition; 79(1): pp. 135-160; Apr. 30, 2001.
Penzel et al.; Dynamics of Heart Rate and Sleep Stages in Normals and Patients with Sleep Apnea; Neuropsychopharmacology; 28(S1); pp. S48-S53; Jul. 1, 2003.
Piquet et al.; Supraorbital transcutaneous neurostimulation has sedative effects in healthy subjects; BMC Neurology; 11(1); p. 135; (manual transcript, 8 pages); Oct. 28, 2011.
Plewnia et al.; Enhancement of human cortico- motoneuronal excitability by the selective norepinephrine reuptake inhibitor reboxetine; Neuroscience Letters; 330(3); pp. 231-234; Sep. 27, 2002.
Pusch et al.; Electrical stimulation of the vestibular system prevents postoperative nausea and vomiting; Acta Annesthesiol Scand.; 44(9); pp. 1145-1148; Oct. 2000.
Riemann et al.; The hyperarousal model of insomnia: A review of the concept and its evidence; Sleep Medicine Reviews; 14(1); pp. 19-31; Feb. 28, 2010.
Rill et al.; Pedunculopontine arousal system physiology—implications for insomnia; Sleep Science; 8(2); pp. 92-99; Jun. 30, 2015.
Rohleder et al.; Psychosocial stress-induced activation of salivary alpha-amylase: an indicator of sympathetic activity; Annals of the New York Academy of Sciences; 1032(1); pp. 258-263; Dec. 1, 2004.
Sara; The locus coeruleus and noradrenergic modulation of cognition; Nature Reviews Neuroscience; 10(3): pp. 211-223. Mar. 1, 2009.
Schmidt et al.; Adrenaline rush: the role of adrenergic receptors in stimulant-induced behaviors; Molecular Pharmacology; 85(4): pp. 640-650; Apr. 1, 2014.
Seugnet et al.; Identification of a biomarker for sleep drive in flies and humans; Proceedings of the National Academy of Sciences; 103(52); pp. 19913-19918; Dec. 26, 2006.
Shiozawa et al.; Transcutaneous vagus and trigeminal nerve stimulation for neuropsychiatric disorders: a systematic review; Arquivos de neuro-psiquiatria; 72(7): pp. 542-547; Jul. 2014.
Siegel; Brain mechanisms that control sleep and waking. Naturwissenschaften; 91(8); pp. 355-365; Aug. 1, 2004.
Somana et al.; Cerebellar afferents from the trigeminal sensory nuclei in the cat. Brain Res.; 38(1); pp. 57-64; Jan. 1980.
Strassman et al; Response of brainstem trigeminal neurons to electrical stimulation of the dura; Brain Research; 379(2): pp. 242-250; Aug. 6, 1986.
Tanaka et al.; Salivary alpha-amylase and cortisol responsiveness following electrically stimulated physical stress in bipolar disorder patients; Neuropsychiatric Disease and Treatment; 8; pp. 1899-1905; Jan. 1, 2013.
Thoma et al.; Acute stress responses in salivary alpha-amylase predict increases of plasma norepinephrine; Biological Psychology; 91(3): pp. 342-348; Dec. 31, 2012.
Tremblay et al.; Uncertain Outcome of Prefrontal tDCS; Brain Stimulation; 7(6): pp. 773-783; Dec. 31, 2014.
Trevizol et al.; Trigeminal Nerve Stimulation (TNS) for Generalized Anxiety Disorder: A Case Study; Brain Stimulation; 8(3): pp. 659-660; Jan. 1, 2015.
Trevizol et al.; Trigeminal Nerve Stimulation (TNS) for Post-traumatic Stress Disorder: A Case Study; Brain Stimulation; 8(3): pp. 676-678; Jan. 1, 2015.
Tyler et al.; Transdermal neuromodulation of noradrenergic activity suppresses psychophysiological and biochemical stress responses in humans; Scientific Reports; 5; (manual transcript, 22 pages); Feb. 8, 2015.
Upadhyay et al.; Noninvasive mapping of human trigeminal brainstem pathways; Magnetic Resonance in Medicine; 60(5): pp. 1037-1046; Nov. 1, 2008.
Van Stegeren et al.; Salivary alpha amylase as marker for adrenergic activity during stress: effect of betablockade; Psychoneuroendocrinology; 31(1); pp. 137-141; Jan. 31, 2006.
Voisin et al.; Nociceptive stimulation activates locus coeruleus neurones projecting to the somatosensory thalamus in the rat; The Journal of Physiology; 566( 3); pp. 929-937; Aug. 1, 2005.
Voss et al.; Induction of self awareness in dreams through frontal low current stimulation of gamma activity; Nature Neuroscience; 17(6); pp. 810-812; Jun. 1, 2014.
Watson et al.; Development and validation of brief measures of positive and negative affect: the PANAS scales; Jouranl of Personality and Social Psychology; 54(6); pp. 1063-1070; Jun. 1988.
Weiss et al; Validity of Activity-Based Devices to Estimate Sleep; Journal of Clinical Sleep Medicine : 6(4); pp. 336-342; Aug. 2010.
Tyler et al.; U.S. Appl. No. 15/460,138 entitled "Systems and methods for transdermal electrical stimulation to improve sleep," filed Mar. 15, 2017.
Goldwasser et al.; U.S. Appl. No. 15/601,394 entitled "Transdermal electrical stimulation at the neck to induce neuromodulation," filed May 22, 2017.
Goldwasser et al.; U.S. Appl. No. 15/967,576 entitled "Transdermal electrical stimulation at the neck," filed Apr. 30, 2018.

\* cited by examiner

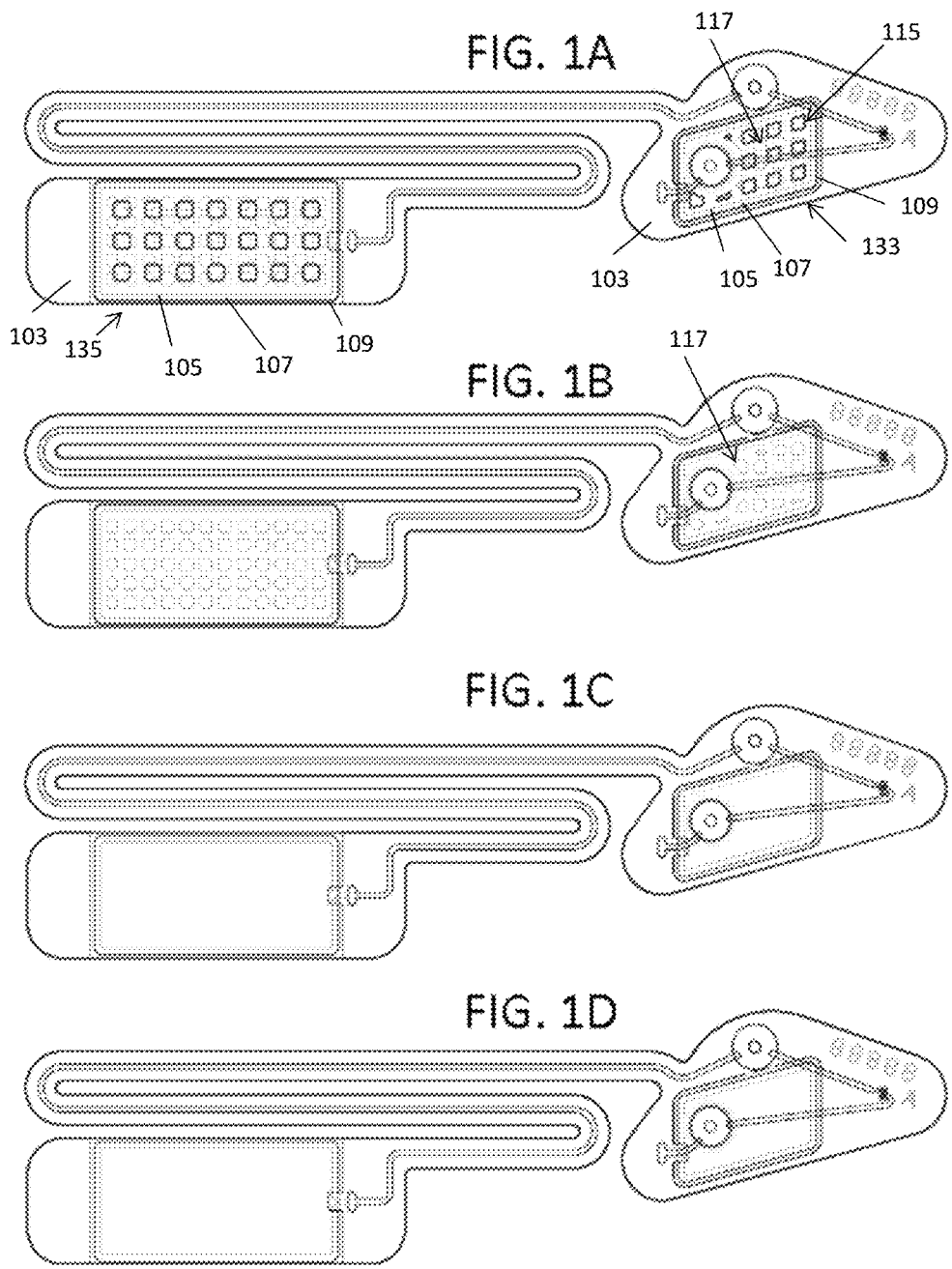

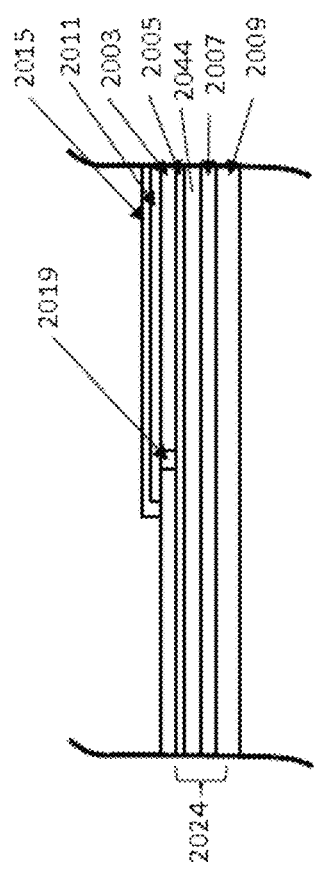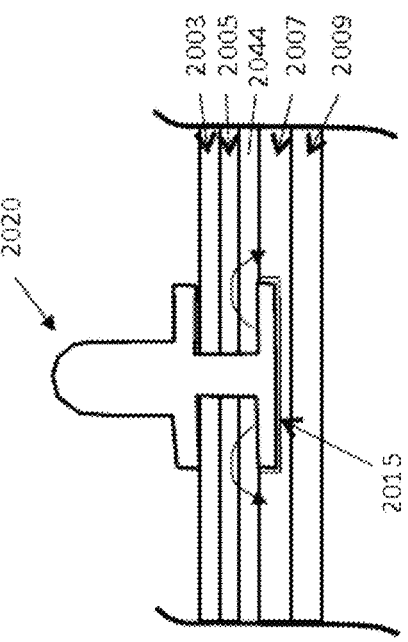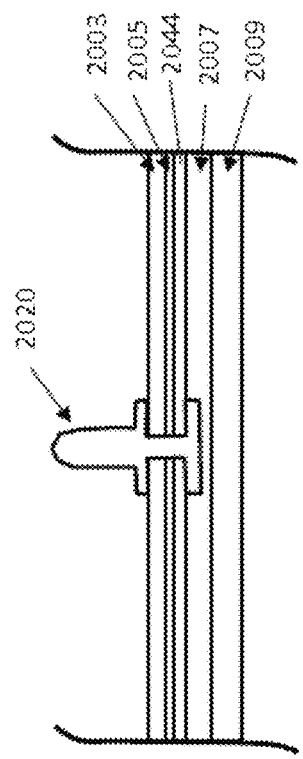
FIG. 12D
FIG. 12F
FIG. 12E

ELECTRODES HAVING SURFACE EXCLUSIONS

CROSS REFERENCE TO RELATED APPLICATIONS

This patent application claims priority to U.S. Provisional Patent Application No. 62/267,290, filed Dec. 15, 2015, titled "TRANSDERMAL ELECTRODES WITH EXCLUSIONS TO IMPROVE UNIFORMITY OF CURRENT DISTRIBUTION", herein incorporated by reference in its entirety.

This application may be related to one or more of: U.S. Provisional Patent Application No. 62/099,950, filed Jan. 5, 2015, titled "CANTILEVER ELECTRODES FOR TRANSDERMAL AND TRANSCRANIAL STIMULATION"; PCT Application No. PCT/US2015/031966, filed May 21, 2015, titled "CANTILEVER ELECTRODES FOR TRANSDERMAL AND TRANSCRANIAL STIMULATION", Publication No. WO 2015/183690; PCT Application No. PCT/US2014/044870, filed Jun. 30, 2014, titled "TRANSDERMAL ELECTRICAL STIMULATION DEVICES AND METHODS FOR MODIFYING OR INDUCING COGNITIVE STATE", Publication No. WO 2014/210595; and PCT Application No. PCT/US2015/031424, filed May 18, 2015, titled "WEARABLE TRANSDERMAL NEUROSTIMULATORS", Publication No. WO 2015/183620, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein relate to electrodes for use in humans and non-human animals. These apparatuses may be used for transdermal stimulation or may be implanted. In particular, described herein are transdermal electrodes that improve the comfort and efficacy of transdermal electrical stimulation (including transdermal electrical neuromodulation).

BACKGROUND

Electrical stimulation of biological tissue in humans and non-human animals has applications for stimulating excitable tissue (neurons, muscle, cardiac tissue, etc.) in both transdermal (i.e. transcutaneous) and implanted configurations. Electrodes that improve the comfort, targeting, and/or efficiency of electrical stimulation of tissue are desired so that more precise, more comfortable, more long-lasting, and/or more power-efficient stimulation can be achieved.

Ideally, transdermal electrical stimulation electrodes deliver current in a manner that minimizes skin irritation and pain to the user or patient. Techniques for improving the comfort and safety of transdermal electrical stimulation including using electrodes that (more) evenly distribute current across the dermal-facing side of the electrode and/or incorporate materials that cause electrochemical reactions to occur within the electrode rather than on or near the user's skin. When current across the face of a dermal electrode is not uniform, current and voltage gradients are created on a user's skin and underlying tissue, causing irritation and/or discomfort. Moreover, charge imbalanced electrical stimulation waveforms generally lead to a charge-transfer regime wherein reduction-oxidation reactions occur; electrodes designed with materials (e.g., Ag—AgCl and hydrogel) so that these reactions occur in electrode layers rather than on or near the user's skin can mitigate irritation and pain, at least in part due to reducing or eliminating pH changes occurring on a user's skin.

Multi-layer electrodes may also improve the comfort of electrical simulation by increasing the uniformity of current distribution and buffering pH changes at or near the skin through redox electrochemistry in the electrodes. Multi-layer electrodes deposited onto a flexible substrate are described in U.S. Pat. No. 9,393,401, U.S. Pat. No. 9,474,891, U.S. Pat. No. 9,333,334, and PCT Patent Application No. PCT/US2015/031966, filed May 21, 2015, titled "CANTILEVER ELECTRODES FOR TRANSDERMAL AND TRANSCRANIAL STIMULATION", Publication No. WO 2015/183690. These multi-layer electrodes significantly improve comfort of transdermal stimulation and may thus improve the efficacy and/or enjoyment of transdermal electrical neuromodulation and other forms of therapeutic or non-therapeutic transdermal electrical stimulation.

It has also been suggested that electrodes having an increased number of edges may provide an improvement in implantable electrodes. See, e.g., Golestanirad et al., ("Analysis of fractal electrodes for efficient neural stimulation", Frontiers in Neuroengineering, Jul. 12, 2013). These electrodes are configured to provide an irregular current density profile on their surface.

When the distribution of current in Ag/AgCl electrodes such as those described above is uneven, e.g., concentrated at the edges or boundaries of the electrode, the uneven distribution causes AgCl to oxidize into Ag at the edges of the electrodes, resulting in a halo of discoloration after usage (charge transfer) and potential reduction in both uniformity of charge distribution across the electrode face and pH regulating consumptive layer function, which may lead to reduced comfort or efficacy of transdermal electrical stimulation. There is a need for electrodes that more evenly distribute current across the face of a dermal electrode to improve the comfort and safety of electrical stimulation, particularly with higher current-density electrodes, including those described by Golestanirad.

Described herein are apparatuses (e.g., devices and systems), and methods that may address at least the needs identified above.

SUMMARY OF THE DISCLOSURE

Described herein are electrodes that, counterintuitively, achieve increased uniformity of current distribution by reducing the uniformity of the electrode used to deliver the current (i.e. by incorporating exclusions, grids, or other patterns to a conductive layer of the electrode).

For transdermal stimulation, the electrodes described herein may balance the total current delivered with a limited current density per unit area which generally defines the comfort profile of the electrode with regard to skin irritation or discomfort. Whereas prior art electrodes (including those incorporating voids or inclusions, teach increasing the "edginess" of electrodes to increase the local variation of current density, such electrodes may result in discomfort. Even traditional transdermal electrodes that are generally uniform and contiguous across a dermal-facing surface are lacking in part due to unwanted variation in current density.

Described herein are transdermal electrode apparatuses and methods of using them that deliver current more uniformly across a dermal facing electrode for improving comfort and efficacy of transdermal electrical stimulation.

Also described herein are electrodes having a multi-layer design. Relative to single-layer designs, multi-layer electrode designs can achieve greater edge-length (e.g., "edginess") per unit area, because conductive elements at an outermost (i.e., interfacing to the targeted biological tissue) layer do not need to be contiguous; gaps may be present between isopolar electrode elements that are conductively coupled through an underlying electrode layer. Single-layer electrode designs for both implanted and transdermal electrode configurations may be limited by the contiguity requirement of single-layer isopolar electrodes; the electrodes described herein may avoid these limitations.

The electrodes described herein may also provide uniform charge transfer and, for some electrode materials, electrochemical (pH) buffering while also reducing the amount of expensive electrode materials such as those containing silver. Typically, transdermal and implanted electrodes undergo chemical reactions during stimulation, limiting the duration of their effective use. For transdermal electrodes, the cost of consumable (i.e. limited use) transdermal electrodes is a limiting factor for some applications. For implanted electrodes, electrode degradation may require an otherwise unwarranted invasive procedure (with associated cost and risk to the patient). The more uniform charge transfer available from the electrodes described herein may be beneficial for improving the useful lifetime of both external and implanted electrodes.

Traditionally, contiguous layers of electrode materials are used in transdermal electrodes. The electrodes described herein may comprise one or more layers with exclusions or other patterns that incorporate gaps or holes so that an electrode layer does not cover the entire electrode face while still maintaining equal (or improved) uniformity of current. This may provide increased efficiencies in electrode manufacturing by reducing the amount of electrode material required to cover a particular area (and effectively stimulate a biological target) and may allow an increased usable lifetime for implanted electrodes.

For example, described herein are electrodes for transdermal electrical stimulation, which may include: a substrate (e.g., a planar substrate); and a multi-layered active electrode region comprising: a first layer on the substrate comprising an electrically conductive layer (e.g., a silver layer) that is arranged in a pattern (e.g., a contiguous pattern in which the parts contact or directly connect) forming a plurality of one or more of: branches and voids (e.g., a grid pattern, a snowflake pattern, a fractal pattern, etc.), a second layer (e.g., comprising a conductive carbon layer) on the first layer, a third layer (e.g., comprising a Ag/AgCl conductive layer) on the second layer, and a hydrogel covering the third layer, wherein the second layer is sandwiched between the first and third layers and has a resistivity that is 5× or greater (e.g., 10×) than the resistivity of the first and/or third layers; wherein the ratio of edges formed by first layer to the perimeter of the multi-layered active region is greater than 4 (e.g., greater than 10, greater than 15, greater than 20, etc.). The third layer may also include the same or a different pattern forming a plurality of one or more of: branches and voids.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A is a schematic showing a multi-layer electrode assembly comprising offset grid-pattern exclusions in both the Ag and Ag—AgCl layers.

FIG. 1B is a schematic showing a multi-layer electrode assembly comprising grid-pattern exclusions in the Ag layer only.

FIG. 1C is a schematic showing a multi-layer electrode assembly with no electrode exclusions on any layer while also using only a single pass of Ag—AgCl (thus thinner), and controlling for totally deposited Ag on the electrode face.

FIG. 1D is a schematic showing a multi-layer electrode assembly control design with no exclusions and a more standard multiple pass Ag—AgCl layer.

FIG. 12D illustrates another example (not to scale) of a section view though an active region of an electrode fed by a conductive trace; in this example, the active region includes a weakly insulating layer (e.g., a thin carbon layer between the silver and silver chloride layers).

FIG. 12E shows a section view though an active region directly connected to a (snap) connector for coupling to a neurostimulator and including a weakly insulating layer (e.g., carbon).

FIG. 12F is a slightly enlarged view of FIG. 12E.

DETAILED DESCRIPTION

Described herein are electrodes in which one or more conductive layers has exclusions (e.g. has a grid design or other pattern) to achieve more even charge distribution across the face of the electrode than if there were a contiguous layer or layers. In general, these electrodes may be used transdermally to stimulate the nervous system, muscles, etc.—or multi-layer electrodes with exclusions in a conducting layer may be implanted for directed stimulation in a patient. An unexpected and key insight underlying the electrode apparatuses described herein (and methods for using them) is that decreasing the uniformity of a conductive layer of an electrode can lead to increased uniformity of the current delivered from the electrode. The core principle underlying this electrode design is that current density is higher at an edge of a conductive area, so designs that increase the edge-length per unit area increase the overall uniformity of current density. Several benefits follow from uniform current densities, including greater control of current density in general (including peak, minimum, average, and spatial distribution of current), improved comfort (i.e. for transdermal stimulation, by removing current gradients that are known to induce irritation, discomfort, and pain), and more even degradation of electrode materials (including consumption of electrode materials in reduction-oxidation reactions for charge imbalanced waveforms) that leads to a longer duration of usable lifetime for a given electrode.

Figure 2A:
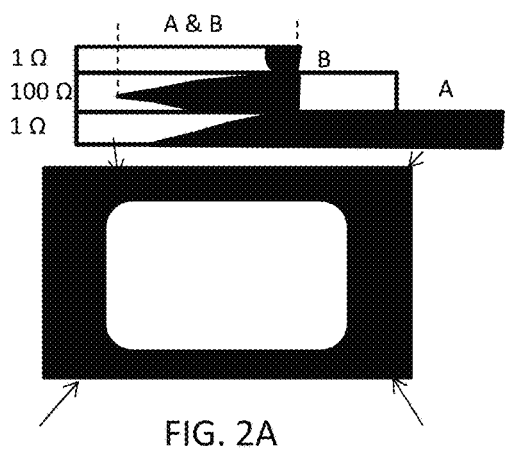
FIG. 2A is a sketch of the density of current for an electrode edge in which multiple layers differ in impedance and are offset in position relative to each other.
Figure 2B:
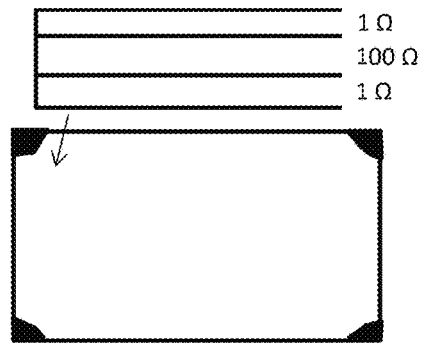
FIG. 2B is another sketch of the direction of current flow in a multi-layer electrode in which multiple layers differ in impedance and are offset in position relative to each other.
Figure 2C:
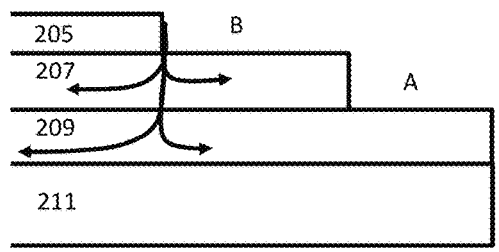
FIG. 2C is a sketch showing exemplar materials for the layers in FIGS. 2A, 2B, 2D, and 2E. (Note that the orientation is flipped relative to FIGS. 2A, 2B, 2D, and 2E; the skin is at the top of FIG. 2C).
Figure 2D:
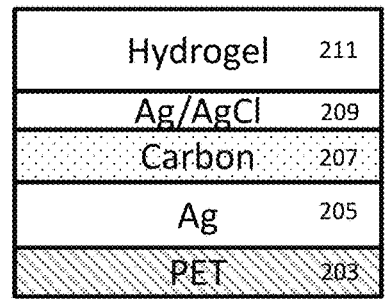
FIG. 2D is a sketch illustrating how current may become concentrated in the corners of a rectangular-shaped multi-layer electrode.
Figure 2E:
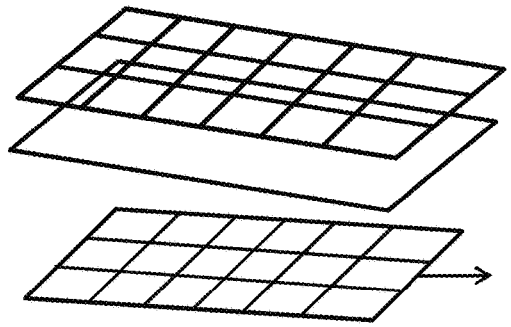
FIG. 2E is a sketch illustrating how multiple layers (the Ag and Ag—AgCl layers) may have grid pattern designs. In some embodiments, the exclusions forming the grids may be aligned to each other across layers, whereas in other embodiments the exclusions may be offset.

The multi-layer electrode design shown in FIGS. 2A-2E schematically illustrates the principle of charge bias toward the edges of an electrode. This layering design is discussed at greater length below (and shown in FIGS. 11A-11B and 12A-12F). FIG. 2D illustrates an electrode stack including: Polyethylene Terephthalate (PET) substrate 203, silver (Ag 205), conductive carbon (207), Ag/AgCl (209), and a dermal-facing hydrogel (211). Whereas the Ag and Ag/AgCl layers have low impedance (e.g., ~1 ohm/cm$^2$), the conductive carbon layer between them has an impedance ~100× higher. Even without the voids or exclusions described herein, this layering design improves the distribution of charge away from the edges (corners) of an electrode to some degree as illustrated in FIGS. 2A and 2B. An offset at the edges of each layer (relative to adjacent layers) may further enable charge to distribute away from the edges. In the examples of FIGS. 2A-2E, the first Ag layer has the least area, the subsequent conductive carbon layer extends beyond the edge of the first Ag layer around its entire circumference, and the third Ag/AgCl layer has the largest area and extends beyond the conductive carbon layer around its entire circumference. Although the layers in FIGS. 2A-2E are shown as "flat" they may bend over each other at the edges (e.g., the overlapping edges from the larger layers may enclose/cover the larger layers. As shown in FIGS. 2A and 2B, these offsets may cause the highest current density (arrows) to occur at the edge of the Ag layer and from this edge towards the middle in the conductive carbon layer. Finally, once the charge enters the Ag/AgCl layer 209, it passes through the hydrogel 211 into the skin (not shown) with sufficiently low impedance that the charge cannot concentrate as highly in the edge of the Ag/AgCl layer as occurred in the Ag layer passed through previously. Although current density in the layer towards the user's skin (at the bottom of the figure) is concentrated at the edge, the concentration away from the edge of the electrode is higher than it would otherwise be without the impedance mismatch of the layers and their spatial offset. In contrast, FIG. 2B shows how current density (darker region) is highly concentrated in the edge of a hypothetical electrode that does not have an offset between the layers.

Despite the improved charge distribution of the offset layer design, the charge uniformity may be further improved as described herein to achieve enhanced stimulation comfort (e.g. for transdermal stimulation) or to uniformly consume or degrade the electrode material. For example, a grid design for the Ag and Ag/AgCl layers (FIG. 2E) offers a further improvement in uniformity of current distribution and is described in further detail below.

Thus, described herein are layered electrodes including a first conductive layer (e.g., an Ag layer) and a second conductive layer (e.g., sacrificial layer such as an Ag/AgCl layer) separated by a weakly insulating layers (e.g., Carbon layer), in which the conductive layer(s) are designed with exclusions (also referred to as gaps or voids) to create more edges across the face of the electrode. The edges of the second conductive layer may overlap the edges of the weakly insulating layer and the edges of the weakly insulating layer may overlap the edges of the first conductive layer; in some variations, the surface area of the first conductive layer is less than the surface area of the weakly insulating layer and the surface area of the weakly insulating layer is less than the surface area of the second conductive layer. Without being bound by theory, current (electrons) tends to be present at greater density at the edges of electrodes at equilibrium. Thus electrodes that include more edges may surprisingly have a greater uniformity of charge distribution despite reduced overall electrode active area, particularly where the multi-layered configuration described herein may spread out the current, resulting in improved comfort for the user (e.g., patient). As a result, stronger electrical stimulation effects (e.g., cognitive effects of transdermal electrical neuromodulation targeting peripheral nerves in the face, neck, or other part of the body) can be achieved by reducing pain or distraction in the user and/or by permitting the user to comfortably attain higher stimulation intensities. Another advantage of electrodes designed with gaps or exclusions (relative to those with contiguous electrode layer(s)) is a reduction in material cost, which can be significant, because biological electrodes commonly include precious metals (e.g. Ag and AgCl, gold, platinum, etc. due to their beneficial electrochemical properties).

Thus, the electrodes described herein may be more effective (and/or comfortable) when used for electrical stimulation of tissue (including stimulation delivered transdermally and stimulation delivered via implanted electrodes) at reduced cost based on a surprising design constraint: improve uniformity of charge distribution by reducing the uniformity of one or more layers of the electrode (e.g., by incorporating voids, e.g., grids, or a fractal-like pattern to increase the length of edges). The increased edge length achieved by using voids, and patterns as described herein may be expressed as a ratio of edge lengths to the outside perimeter of the electrode, or as the ratio of edge length(s) to surface area for the entire electrode (e.g., the entire electrode may refer to the electrode receiving a single electrical input/output). This ratio (e.g., length of edges/length of outside perimeter) is typically greater than 1 (e.g., greater than 1.2, greater than 1.5, greater than 2, greater than 3, greater than 4, greater than 5, greater than 6, greater than 7, greater than 8, greater than 9, greater than 10, greater than 11, greater than 12, greater than 13, greater than 14, greater than 15, greater than 16, greater than 17, greater than 18, greater than 19, greater than 20, greater than 25, greater than 30, etc.).

Various designs can be used to improve or optimize the uniformity of current distribution, including one or more exclusion design feature selected from the list including but not limited to: a single exclusion, a plurality of exclusions, exclusions that are all the same size or exclusions that vary in size (i.e. smaller exclusions and thus more dense set of edges toward the center of an electrode), a grid pattern of identical or similar shapes, different shapes of exclusions, a radial pattern in which exclusions are small near the center of the extending radii and larger near the periphery of the electrode, exclusions on one layer of an electrode or exclusions on multiple electrode layers, and exclusions shaped as polygons, circles, ovals, fractal patterns, etc.

Transdermal electrodes that have gaps, holes, or other patterns may also reduce cost of electrode materials (which may be expensive, i.e. silver) while also increasing the edge-length of electrode area per unit area to achieve increased uniformity of current distribution, cause chemical reactions in the electrode to occur more evenly across the electrode area, and improve the comfort and efficacy of stimulation.

In general, electrode layer (e.g. Ag or Ag—AgCl layer) patterns that have gaps, exclusions, voids, or other patterns whereby the layer does not extend fully across the electrode region require a balance between (1) having sufficient coverage of the conducting layer and (2) incorporating gaps between portions of the conducting layer across the face of the electrode in order to create increased edge-length per unit area of the electrode. Thus, exemplar electrodes of this invention provide sufficient conductive electrode area for bulk electrochemistry reactions to occur in a non-limiting (or minimally-limiting) fashion while at the same time increasing the available edges for current to distribute and thus achieve a more even spread of current across the face of an entire electrode.

In general, one benefit of the electrode apparatuses described herein (particularly those comprising consumptive pH buffering conductive layers, e.g. Ag—AgCl layers) is that the increased uniformity of charge transfer causes electrochemical reactions to occur more uniformly across the electrode area, permitting a thinner layer of electrode material to be used (for a given amount of pH buffering reactions) than if the charge were concentrated at the edges of the electrode as is generally the case for electrodes lacking the voids or exclusions described herein. In the exemplar electrodes shown schematically and in images in FIGS. 5A-11B, the electrode layers may be deposited by a silk-screen like process. In general, it may be difficult to design or implement a layer of variable thickness (i.e. such that more Ag—AgCl was deposited in the corners of an electrode, where they would be consumed more quickly). Due to this fundamental physical limitation, the design described herein is preferred, because it achieves more consumptive pH buffering with less of the expensive silver-containing electrode material. In general, two factors contribute to savings on materials for a consumptive conducting layer: a thinner layer achieves more electrochemical buffering due to the more even spread of current across the face of the electrode, and no material needs to be deposited in the gaps (e.g., voids) between conductive electrode regions (i.e. in the voids of a grid as in FIGS. 3-4 and FIG. 10E or the circuitous gaps between active electrode areas in the 'snowflake' pattern of FIGS. 5B, 6A, 7C, 8B, 9C, 10A-10C, 14) so that the total area of that electrode layer is reduced.

Electrode apparatuses as described herein may be electrically coupled to a neurostimulator device for delivering controlled current across two or more electrode areas, including neurostimulator systems for implantable and transdermal electrical stimulation known in the art. For example, a wearable neurostimulator controllable from a user computing device (e.g. smartphone) is described in U.S. Pat. No. 9,002,458 titled "TRANSDERMAL ELECTRICAL STIMULATION DEVICES FOR MODIFYING OR INDUCING COGNITIVE STATE" issued on Apr. 7, 2015 and methods of using a wearable neurostimulator is described in U.S. Pat. No. 9,014,811 with the same title and issued on Apr. 21, 2015.

The several figures show example electrodes designed for transdermal electrical neuromodulation delivered to a user's temple and neck area or temple and mastoid area. The systems and methods for inducing cognitive effects from electrical stimulation through these sites (with electrodes having uniform and contiguous layers) are described in PCT Application No. PCT/US2014/044870, filed Jun. 30, 2014, titled "TRANSDERMAL ELECTRICAL STIMULATION DEVICES AND METHODS FOR MODIFYING OR INDUCING COGNITIVE STATE", Publication No. WO 2014/210595; and PCT Application No. PCT/US2015/031424, filed May 18, 2015, titled "WEARABLE TRANSDERMAL NEUROSTIMULATORS", Publication No. WO 2015/183620, incorporated fully herein by reference. The flexible electrode design, including electrode layers and electrical connection traces, is described in U.S. Provisional Patent Application No. 62/099,950, filed Jan. 5, 2015, titled "CANTILEVER ELECTRODES FOR TRANSDERMAL AND TRANSCRANIAL STIMULATION"; U.S. Provisional Patent Application No. 62/099,977, filed Jan. 5, 2015, titled "FLEXIBLE ELECTRODE DEVICES FOR TRANSDERMAL AND TRANSCRANIAL ELECTRICAL STIMULATION"; and PCT Application No. PCT/US2015/031966, filed May 21, 2015, titled "CANTILEVER ELECTRODES FOR TRANSDERMAL AND TRANSCRANIAL STIMULATION", Publication No. WO 2015/183690, herein incorporated by reference in their entirety.

Figure 11A:
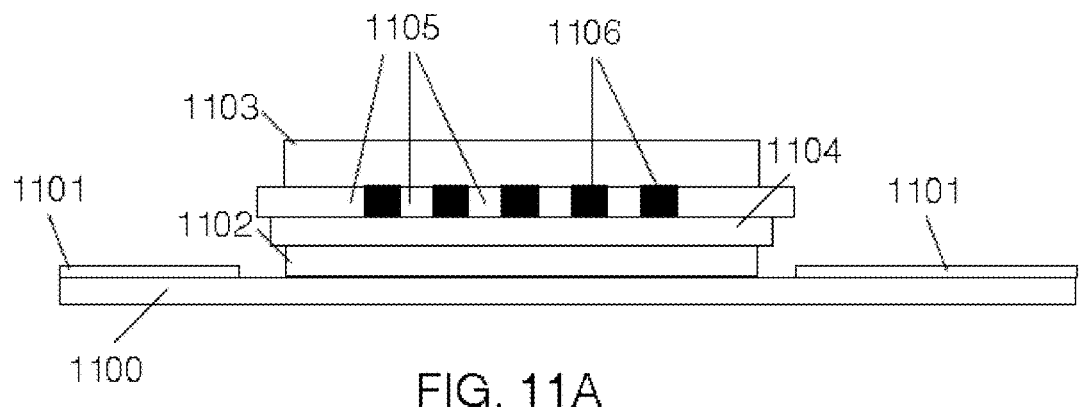
FIG. 11A shows an exemplary (not to scale) sectional view through an active region of a multi-layer electrode fed by a conductive trace comprising gaps in a Ag—AgCl layer.
Figure 11B:
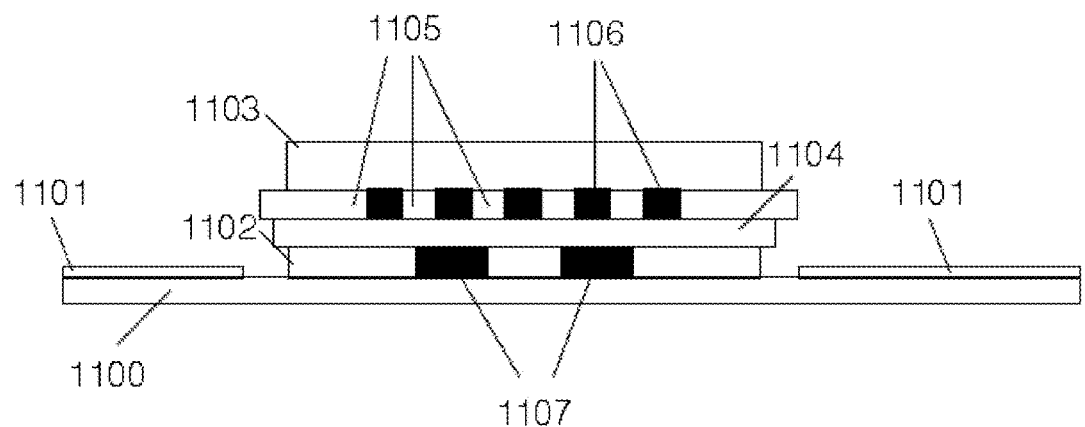
FIG. 11B shows an exemplary (not to scale) sectional view through an active region of a multi-layer electrode fed by a conductive trace comprising gaps in a Ag—AgCl layer and a Ag layer.

An electrode design for a flexible transdermal electrical stimulation electrode is illustrated schematically in FIGS. 11A and 11B in cross section (not to scale). FIGS. 11A and 11B illustrate a flexible (i.e. PET) substrate 1100 over which an insulating dielectric 1101 is coated, except over the electrode area. The first electrode layer (first conductive layer) is silver 1102. The second layer is a weakly conductive electrode layer (weakly insulating layer) such as conductive carbon 1104. The third layer (e.g., the second conductive layer) is Ag/AgCl 1105, which is designed so that there are voids 1106 (only some of the voids are labeled) to increase the edge-length per unit area and improve the uniformity of current density delivered into hydrogel 1103 and the subject's skin (not shown). Whereas FIG. 11A has a uniform first layer 1102, FIG. 11B has voids 1107 in the Ag layer 1102, a design feature which can further improve the 'edginess' of the electrode and the uniformity of charge transfer (in this case by causing charge to be distributed more evenly in the first layer 1102 before passing in subsequent layers 1104, 1105, 1103, then skin).

Figure 12A:
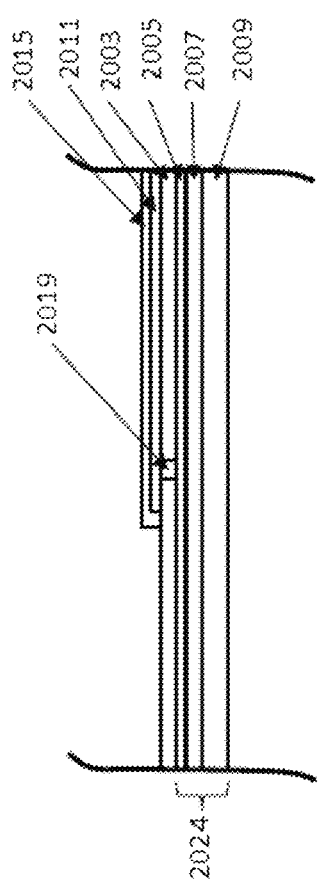
FIG. 12A shows an exemplary (not to scale) sectional view through an active region of an electrode fed by a conductive trace.

FIG. 12A is a section through one variation of an active region of an electrode apparatus, showing different layers that may be used to form the active region. In general, an electrode having an input/output (so that the same electrical signal is applied across the entire electrode) may be referred to as a single active region. The first and/or second conductive regions (e.g., Ag and Ag/AgCl) layers within a single active region may be divided up into branches, grids or any other continuous pattern, as described and illustrated above (e.g., having a ratio of edges of the electrode pattern(s) of the first and/or second electrode layers relative to the outer perimeter of the active region that is greater than x, where x is 1.5, 2, 3, 4, 5, 6, 7, 8, 9, 10, 12, 14, 15, 16, 17, 18, 19, 20, 21, 22, 23, 25, 30, etc.).

For example, in FIG. 12A, an electrode trace 2011 extends on a top surface of a substrate 2003 (such as a polymeric material appropriate for use in a flexible circuit, e.g., Kapton). This trace 2011 may be insulated (e.g., by an insulating covering) 2015. An opening through the flex circuit (e.g., hole 2019) may include a conductive material (e.g., carbon black, silver, etc.) resulting in electrical communication between the trace 2011 and a portion of the electrically active region 2024, that (in this example) includes a layer of conductive metal (e.g., Ag) 2005, a layer of sacrificial conductor (e.g., Ag/AgCl) 2007 that completely covers the Ag layer and an outer, skin-contacting layer of hydrogel 2009 that is in electrical contact with the Ag/AgCl layer, and may also completely cover it (or cover it in conjunction with an insulator). The sacrificial Ag/AgCl layer 2007 in this example may also extend beyond the border of the conductive (i.e. Ag) layer 2005 to avoid shorts between the conductive (i.e. Ag) layer and the skin-contacting layer of hydrogel 2009 (i.e. extends beyond it around its entire circumference, including any internal exclusions or voids in the layer, for instance to permit a snap conductor to be placed).

Figure 12C:
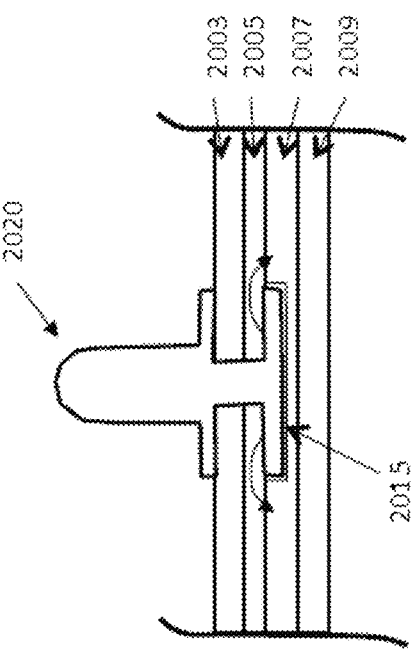
FIG. 12C is a slightly enlarged view of FIG. 12B.
Figure 12B:
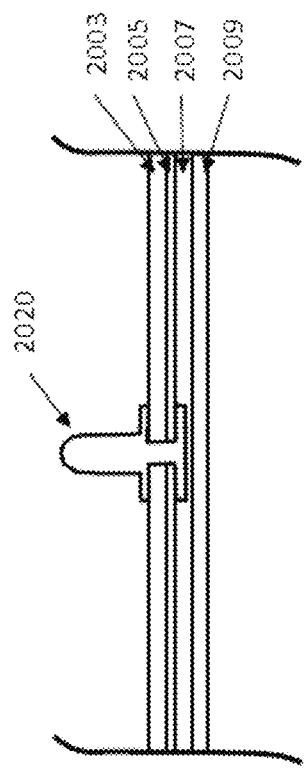
FIG. 12B shows a section view though an active region directly connected to a (snap) connector for coupling to a neurostimulator.

FIG. 12B shows a partial section through a portion of an active region that is electrically connected to an electrical and/or mechanical connector via an indirect connection pathway and thereby connects to an electrical stimulator (e.g., such as a neurostimulator). In some variations the electrode includes an active region that is directly connected to a connector, such as the first active region 133 in FIG. 1A. An example of this arrangement is shown in FIG. 12B and in detail in FIG. 12C.

In FIG. 12B the active region of the electrode includes a contact (shown as a snap or pin) for connection to the electrical stimulator (e.g., neurostimulator). In this example, the connector 2020 penetrates the substrate 2003 and a layer of conductive material (shown as a conductive metal, e.g., Ag) 2005 and makes electrical contact with this Ag layer. The bottom of the post or connector 2020 is electrically insulated (visible in FIG. 12C as the insulating layer 2015). A sacrificial layer of Ag/AgCl covers the Ag layer (and the insulated base of the post 2020), and a skin-contacting layer of conductive hydrogel 2009 contacts the Ag/AgCl layer. FIG. 12C shows a slightly enlarged view of FIG. 12B, and schematically illustrates the current flowing from the electrical/mechanical connector 2020 into the hydrogel 2009 through the sacrificial Ag/AgCl layer 2007 and the Ag conductive layer 2005. In this example, the connection is configured so that the current does not flow directly into the Ag/AgCl 2007 or hydrogel 2009, but first passes from an upper surface of the connector that is in electrical contact with the Ag layer 2005 and then down into the Ag/AgCl layer 2007 and the hydrogel to contact the user. Thus, in this example, the portion of the connector base in contact with the silver/silver chloride layer is insulated 2015 so that the current primarily passes through the silver layer 2005.

In general, an electrically active region of an electrode apparatus may include a non-consumptive conducting layer (e.g., 2005 in FIGS. 12A-12C), a consumptive conducting layer (e.g., 2007 in FIGS. 12A-12C), and a conductive hydrogel layer (e.g., 2009 in FIGS. 12A-12C). In some embodiments, the consumptive layer may be a buffer layer disposed between the non-consumptive layer and the hydrogel layer. Further, the consumptive layer may extend beyond the boundary of the non-consumptive layer at each edge of the non-consumptive layer and may be configured to reduce hydrolysis in the hydrogel layer, such that the consumptive layer donates electrons for redox reactions. Examples of the conductive non-consumptive layers may include silver, gold, copper, or any other type of conductive metal or non-metallic material, such as carbon or conductive polymers (e.g. poly(3,4-ethylenedioxythiophene). Preferably, the non-consumptive and consumptive layers include silver. An important feature of the non-consumptive layer is that any electrochemical reactions occurring in that layer do not cause the quality of the layer as an electrical conductor (i.e. impedance) to change during a transdermal (e.g., transcranial) stimulation. This feature ensures that current delivered to the layer is, for the most part, distributed evenly over its surface first before entering the consumptive layer. In some variations, an additional, higher impedance (e.g., carbon), layer is disposed between the non-consumptive layer and the consumptive layer to more evenly spread current across the non-consumptive layer before entering the higher impedance layer and, subsequently, the consumptive layer. In some embodiments, the non-consumptive layer experiences reduced consumption, such that the non-consumptive layer includes silver. Alternatively, the non-consumptive layer may experience essentially zero consumption, such that the non-consumptive layer includes carbon. In some embodiments, the non-consumptive layer experiences reduced consumption since it does not include an anion that can be electrically consumed during electrical stimulation. The non-consumptive layer may disperse the electrical current over its surface area before the current reaches the consumptive layer (i.e. there is lower impedance within the non-consumptive layer than between the non-consumptive layer and the consumptive layer). If the electrical current is not dispersed over the surface area of the non-consumptive layer before reaching the consumptive layer, the consumptive layer may be over-consumed, such that AgCl becomes Ag(0) in a local area of the consumptive layer surface, causing uneven current distribution and the potential for local hydrolysis and local pH changes that may lead to discomfort in the subject. In embodiments, the consumptive layer is composed of a ratio of silver to silver chloride (Ag:AgCl) for efficient consumption and electrochemistry. Optimal ratios can be selected based on the charge balance of stimulation. In some embodiments, the ratio of Ag to AgCl particles in the consumptive layer may be between 40%:60% to 95%:5%, preferably 65%:35% to 85%:15%. Alternatively, the consumptive layer may include any suitable ratio of Ag:AgCl such that the chloride may be consumed but not depleted during an electrical stimulation session of sufficient length to induce a beneficial cognitive effect in a subject. The AgCl in the consumptive layer is consumed during alternating current or direct current stimulation (DC) because it acts as a sacrificial anode/cathode and is converted to Ag and a Cl$^-$ ion. The Ag+ in the consumptive layer is consumed during alternating current or direct current stimulation (DC) because it acts as a sacrificial anode/cathode and is converted to AgCl. In some embodiments, if the consumptive layer does not fully cover the dermal side of the non-consumptive layer, the current may travel directly to the hydrogel layer and cause a site of high current density, for example a current hotspot. In some embodiments, the conductive hydrogel layer ensures that the current is transmitted substantially evenly to the skin of a user. Further, the hydrogel layer creates a uniform connection between the multi-electrode assembly and the skin of a user.

In any of the electrode apparatuses described herein, an additional layer may be positioned between the conductive layer in electrical contact with the connector (e.g., snap connector) and the sacrificial anode/cathode layer in contact with the hydrogel. The additional layer may be a material that is less conductive than the adjacent conductive metal (e.g., Ag) layer and sacrificial (e.g., Ag/AgCl) layer, or even a weakly insulating material. In this example, the material is carbon, although other materials may be used. In general this layer may be less conductive than the layers immediately above (e.g., Ag) and below (e.g., Ag/AgCl). For example, FIGS. 12D-12F illustrate another variation of a section through an active region of an electrode apparatus, showing different regions that may be used to form the active region and including an additional carbon layer. In FIG. 12D, the electrode trace 2011 extends on a top surface of a substrate 2003 (such as a polymeric material appropriate for use in a flexible circuit). This trace 2011 may be insulated (e.g., by an insulating layer 2015). An opening through the flex circuit (e.g., hole 2019) may include a conductive material (e.g., carbon black, silver, etc.) making an electrical communication between the trace 2011 and a portion of the electrically active region 2024, that includes a layer of conductive metal (e.g., Ag) 2005, a layer (e.g., carbon) having a lower conductance than the adjacent layers 2044, a covering layer of sacrificial Ag/AgCl 2007 that completely covers the Ag layer and is itself covered by the carbon layer 2044, and an outer, skin contacting layer of hydrogel 2009 in electrical contact with the Ag/AgCl layer.

In any of the electrode apparatuses described herein, the first conductive layer (e.g., a Ag layer) connects to the connector (e.g., pin, snap, clamp, etc.) and thus the electrical stimulator. This first conductive layer is separated from the sacrificial layer (e.g., Ag/AgCl layer) that connects to the gel (e.g., hydrogel) by the intermediate, less conductive layer. This less conductive layer may also be referred to as a weakly conductive layer, a weakly insulating layer, or a more resistive layer (all in reference to the adjacent first conductive layer and sacrificial layer). In general, this weakly conductive layer has an electrical conductance that is lower than either the adjacent first conductive layer or the sacrificial layer, although the electrical properties of the sacrificial layer may change with use. Thus, in general the weakly conductive layer may be more resistive than the first conductive layer; for example, the weakly conductive layer may have a resistivity that is greater than 3×, 4×, 5×, 6×, 7×, 8×, 9×, 10×, 15×, 20×, etc., the resistivity of the first conductive layer (e.g., may be between 2× and 1000× the resistance of the conductive layer(s), may be between 2× and 100×, may be between 3× and 100×, may be between 5× and 100×, may be between 10× and 1000×, etc.). In some variations, the resistance of the weakly conductive layer is greater than 5× the resistance of the first conductive layer that it covers. In general, each successive layer distal from the flexible substrate (i.e. a polymeric material appropriate for use in a flexible circuit) extends beyond the edge of the more proximal layer along its entire circumference to ensure that current cannot short between non-successive layers.

The weakly conductive layer may be formed of any appropriate material having the electrical properties described herein. For example, the weakly conductive layer may include carbon. For example, the weakly conductive material may be a polymeric material (including rubbers, polyvinyl chlorides, etc.) that is mixed with or incorporates carbon (e.g., carbon particles), etc.

FIG. 12E shows a partial section through a portion of another active region that is in electrical contact with a connector configured to couple with the electrical stimulator (e.g., the electrical and/or mechanical connector that contacts with the neurostimulator). The electrode may include an active region that is connected to the connector as shown in FIG. 12E and in detail in FIG. 12F. In this example, the active region of the electrode includes a contact (shown as a snap or pin) for connection to the electrical stimulator (e.g., neurostimulator). The connector 2020 penetrates the substrate 2003 as well as a layer of conductive material (shown as a conductive metal, e.g., Ag) 2005 and (in some variations) a layer of less conductive material (e.g., carbon) 2044, to make electrical contact with this Ag layer. The bottom of the post/connector 2020 is electrically insulated (shown in FIG. 12E as an insulating layer 2015). In this example, the Ag layer 2005 is separated from the sacrificial layer of Ag/AgCl 2007 by a less conductive (than either the Ag or Ag/AgCl layers) layer of carbon 2044, and a skin-contacting layer of conductive hydrogel 2009 contacts the Ag/AgCl layer 2007. FIG. 12F shows a slightly enlarged view of FIG. 12E, and schematically illustrates the current flowing from the electrical/mechanical connector 2020 into the hydrogel 2009 through the sacrificial Ag/AgCl layer 2007, less conductive layer 2044 and the conductive Ag layer 2005. In this example, current does not flow directly into the Ag/AgCl 2007 or hydrogel 2009, but first passes from an upper surface of the connector that is in electrical contact with the Ag layer 2005, either directly (not shown) or through the less conductive (e.g., carbon) layer 2044, and then flows down into the Ag/AgCl layer 2007 and the hydrogel to contact the user.

The optional less conductive layer 2044 described above may be helpful to spread the current as it moves from the highly conductive metal layer such as the Ag layer 2005 shown in FIGS. 12A-12F to the sacrificial layer (e.g., Ag/AgCl layer 2007) and into the hydrogel. In effect, this carbon layer (or similar less-conductive layer) may make the electrodes much more comfortable for the user to wear them, even when delivering relatively high intensity current signals, by improving the uniformity of current density and electrochemistry occurring in the consumptive layer and/or hydrogel.

In some embodiments, the electrode apparatus (flexible electrode assembly) may include an adhesive component. The adhesive component may be configured to couple the electrode apparatus to a body portion of a user or any other device or system. An adhesive component may surround and/or be adjacent to the boundary of the consumptive layer. In some embodiments, the adhesive component and the three layers (consumptive, non-consumptive, and hydrogel) of the electrode active region may be substantially the same thickness, such that substantially all areas of the flexible assembly may be flush with the skin of a user. In some embodiments, the hydrogel layer may extend slightly beyond the adhesive layer so that the hydrogel makes a more uniform contact through slight compression when the electrode is adhered to the skin.

Alternatively, a flexible multi-electrode assembly may be pressed against or held to a body portion of a user. In some embodiments, the flexible transdermal multi-electrode assembly may be pressed against a body portion of the user using a headband, helmet, head scarf, or any other type of wearable device.

As described above, a single flexible transdermal assembly may include two or more electrodes (active regions) for electrical stimulation, such that only one assembly is required for electrical stimulation. For example, a user may stimulate a forehead region with a first electrode region (active region) on the flexible transdermal assembly and the back of the neck with a second electrode region (active region) on the same assembly to achieve the desired neuromodulation effect. Alternatively, the system may utilize two separate or separable assemblies, such that each assembly includes one electrode for electrical stimulation. In some embodiments, the two assemblies may be electrically coupled by a coupling element. For example, a user may position one assembly on the forehead and the second assembly on the back of the neck to achieve the desired neuromodulation outcome. Alternatively, any number of electrodes in each assembly may be used to achieve the desired neuromodulation effect. In some embodiments, any number of electrode areas on the same or different assemblies may be coupled by one or more traces. For example, one trace may couple an electrode area on the forehead to an electrode area on the back of the neck. Alternatively, one or more electrode areas on the same or different assemblies may be independently and directly controlled by the controller, for example through pogo pins.

Figure 13:
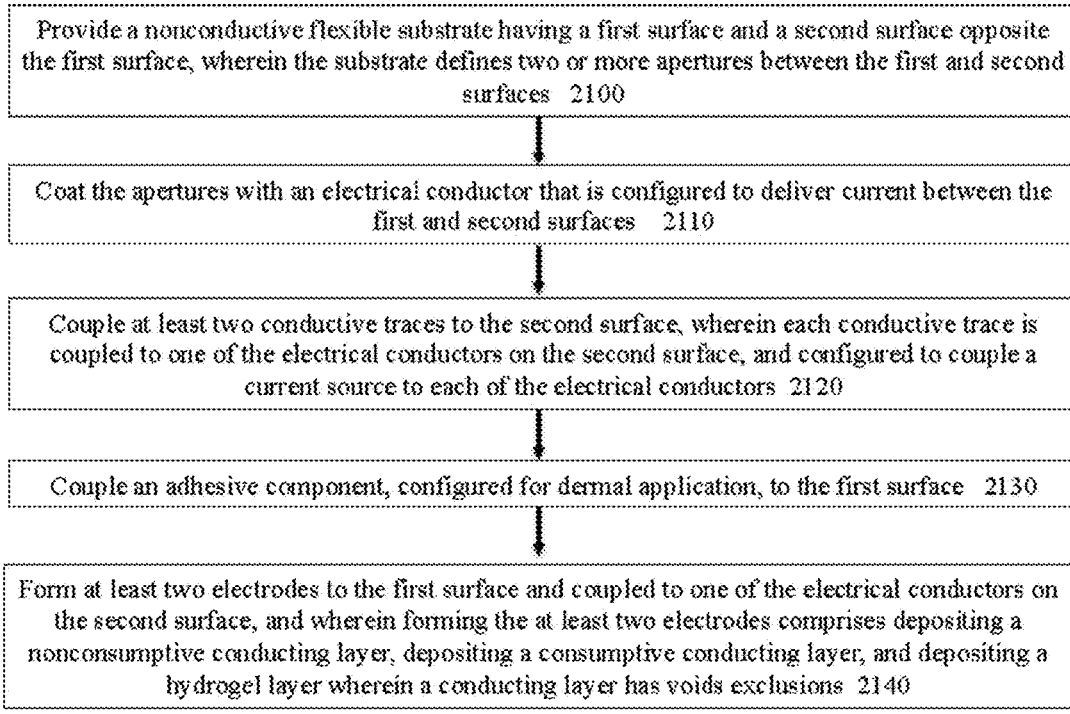
FIG. 13 schematically illustrates one method of forming an electrode apparatus such as a cantilever electrode apparatus.

FIG. 13 illustrates one method of making a flexible electrode apparatus as described herein. In this example a nonconductive flexible substrate 2100 having a first surface and a second surface opposite the first surface and two or more apertures between the first and second surfaces may be coated so that the apertures are at least partially filled (and more preferentially completely filled) with an electrical conductor that is configured to deliver current between the first and second surfaces 2110. Two or more conductive traces may then be formed on the second surface, such that each conductive trace is coupled to one of the electrical conductors on the second surface, and configured to couple a current source to each of the electrical conductors 2120; an adhesive component, configured for dermal application, may then be placed (e.g., coated) to the first surface 2130; and at least two electrodes may be formed or connected to the first surface and coupled to the one of the electrical conductors on the second surface wherein a conducting layer has voids exclusions 2140. Connecting or forming the at least two electrodes may include depositing a non-consumptive conducting layer, depositing a consumptive conducting layer, and depositing a hydrogel layer, such that the consumptive layer is a buffer layer disposed between the non-consumptive layer and the hydrogel layer that extends beyond the boundary of the non-consumptive layer at each edge of the non-consumptive layer and is configured to reduce hydrolysis in the hydrogel layer.

Figure 10A:
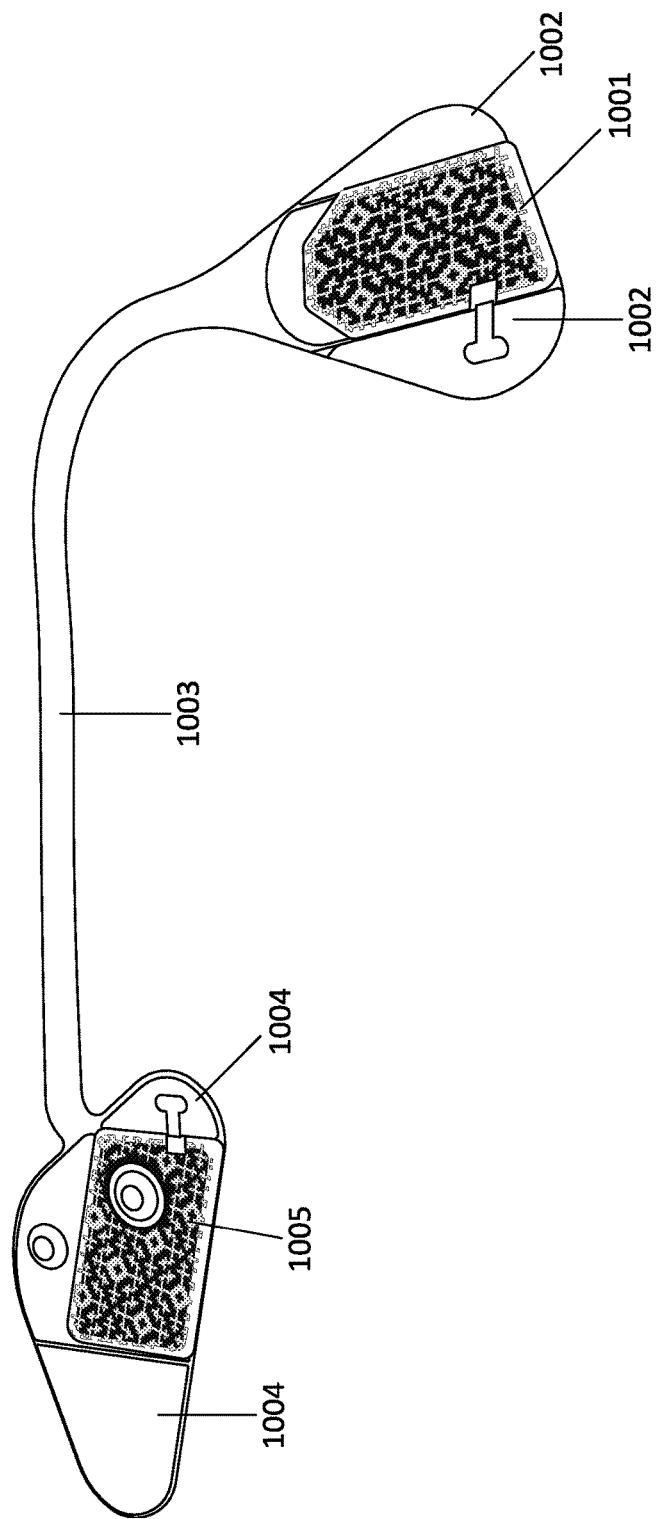
FIG. 10A shows an unused flexible electrode assembly with two multi-layer electrode areas that has a Ag—AgCl layer of a multilayer electrode comprising a 'snowflake' pattern.
Figure 10B:
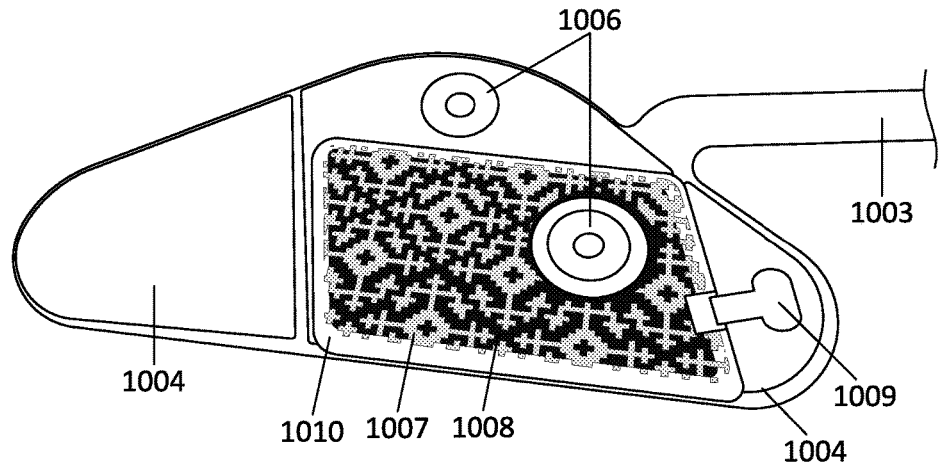
FIG. 10B shows a higher magnification view of one electrode area of an unused flexible electrode assembly that has a Ag—AgCl layer of a multilayer electrode comprising a 'snowflake' pattern.
Figure 10C:
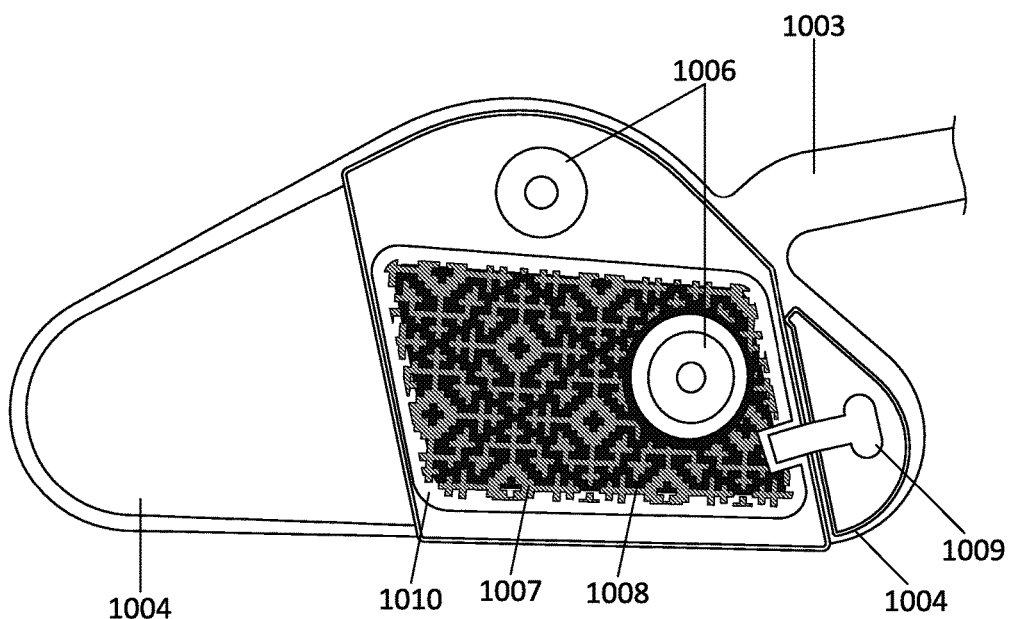
FIG. 10C shows a higher magnification view of one electrode area of a flexible electrode assembly that has a Ag—AgCl layer of a multilayer electrode comprising a 'snowflake' pattern and indicates uniform conversion of AgCl to Ag across the electrode area as indicated by a darkened coloration after use by a subject for transdermal electrical stimulation.
Figure 10D:
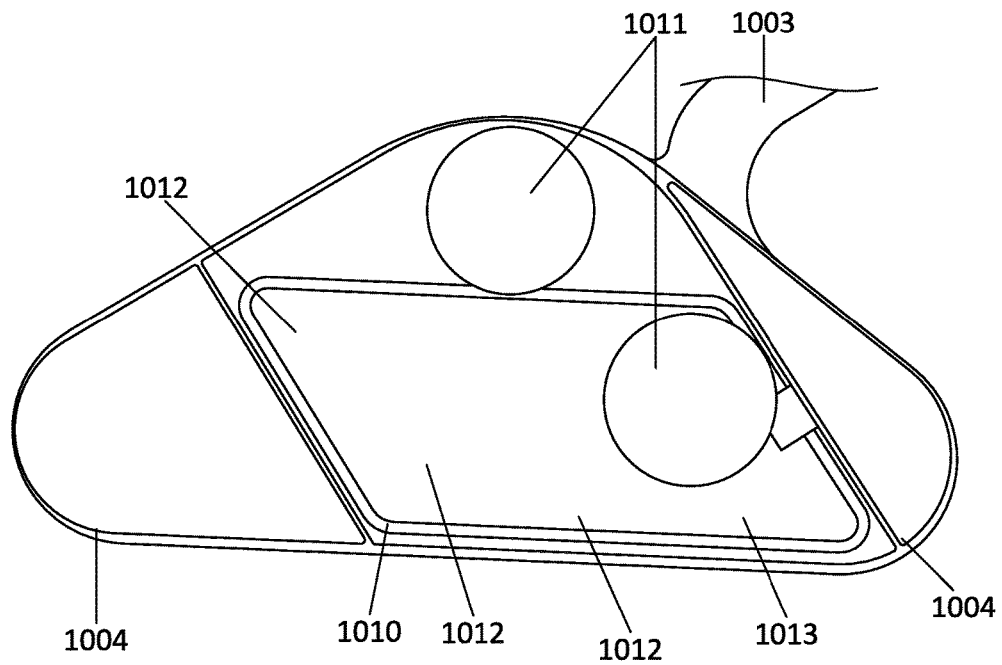
FIG. 10D shows a higher magnification view of one electrode area of a flexible electrode assembly that has a Ag—AgCl layer of a multilayer electrode that is uniform across the electrode area and indicates uneven conversion of AgCl to Ag across the electrode area as indicated by localized regions of darkened coloration after use by a subject for transdermal electrical stimulation.

FIG. 10D shows an example of a multi-layer electrode formed as part of an applicator for TES (e.g., a wearable neurostimulation TES), as described above and shown, only without any voids or exclusions increasing the ratio of inner edge length to outer perimeter edge length. The image view shows only a first electrode area designed for placement with a wearable neurostimulator on the temple area. PET substrate 1003 is a connector region to a second electrode area, while PET substrate areas 1004 have overlying biocompatible adhesive for holding the electrode and neurostimulator unit firmly on the subject's skin. Nonconductive nylon covers 1011 (also refer to FIG. 12C) ensure that current from the conductive snaps on the back side of the electrode (not shown) cannot pass directly to the electrode area and cause a short circuit. Border region 1010 shows bare PET substrate uncoated with dielectric. Note for reference to the discoloration of the electrode area that the dielectric in 10D is black and thus darker than the dielectric used for the prototype electrode assemblies in 10A-C and 10E. After a transdermal electrical stimulation session on a subject's temple using a non-charge balanced (e.g. asymmetric) pulsed waveform, some AgCl in the Ag/AgCl layer has reacted with water in the hydrogel to create Ag, which has a darker color (1012) while other areas of the electrode maintain a light color (1013), indicative of fewer redox reactions having occurred in this area. From this pattern of discoloration, it can be inferred that charge from stimulation was concentrated in the edges and corners of the electrode—and that hot spots in more central areas of the electrode were present. The lack of uniform discoloration in this electrode motivates improved electrode designs to improve current density uniformity. The examples below show improved uniformity of discoloration on the Ag/AgCl layer for electrodes having voids (gaps, patterned exclusions) in this layer.

Example 1: Grid-Style Voids to Improve the Uniformity of Current Distribution in Transdermal Electrodes FIGS. 1A-1D, 3, and 4 show schematic diagrams of active areas of an electrode apparatus comprised of multi-layer electrodes having one or more layer with grid-style exclusions to improve the uniformity of current density across the electrode face.

FIGS. 1A-1D shows line drawings of variations of a flexible electrode apparatus comprising a flexible (PET) substrate 103, a layer of Ag 105, a layer of conductive carbon ink 107 (higher impedance than Ag or AgCl), a layer of Ag—AgCl 109, and a dermally-facing hydrogel (not shown in drawings). These designs were tested in subjects with a transdermal electrical neuromodulation apparatus (as described in PCT Patent Application No. PCT/US2014/044870, filed Jun. 30, 2014, titled "TRANSDERMAL ELECTRICAL STIMULATION DEVICES AND METHODS FOR MODIFYING OR INDUCING COGNITIVE STATE", Publication No. WO 2014/210595; and PCT Patent Application No. PCT/US2015/031424, filed May 18, 2015, titled "WEARABLE TRANSDERMAL NEUROSTIMULATORS", Publication No. WO 2015/183620) and showed that electrode designs with grids were the most comfortable (and thus more effective for inducing a cognitive effect). Electrodes containing grids in one or both layers are a significant improvement for transdermal electrical stimulation.

FIG. 1A is a schematic showing a multi-layer electrode assembly comprising offset grid-pattern exclusions in both the Ag (grid pattern 117) and Ag—AgCl layer (grid pattern 115) of two electrode active areas 135, 133. FIG. 1B is a schematic showing a multi-layer electrode assembly comprising grid-pattern exclusions 117 in the Ag layer only of two electrode areas. FIG. 1C is a schematic showing a multi-layer electrode assembly with no electrode exclusions on any layer while also using only a single pass of Ag/AgCl (thus thinner), and controlling for the thickness of deposited Ag on the electrode face. FIG. 1D is a schematic showing a multi-layer electrode assembly control design with no exclusions and a more standard multiple pass Ag—AgCl layer.

Figure 3:
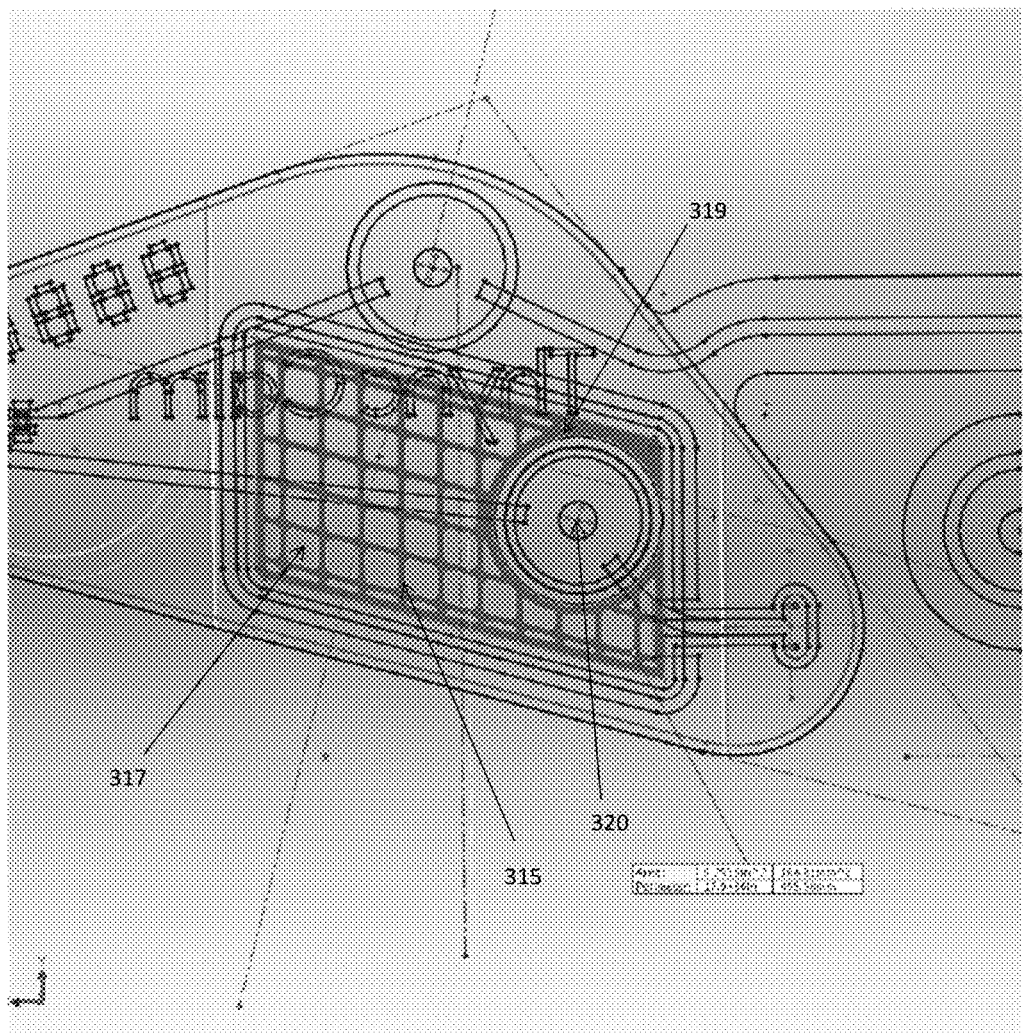
FIGS. 3 and 4 show schematics of two active areas of an electrode apparatus wherein the filled regions contain conductive material and the approximately rectangular (trapezoidal) regions are exclusions, creating extensive edges within the electrode region.
Figure 4:
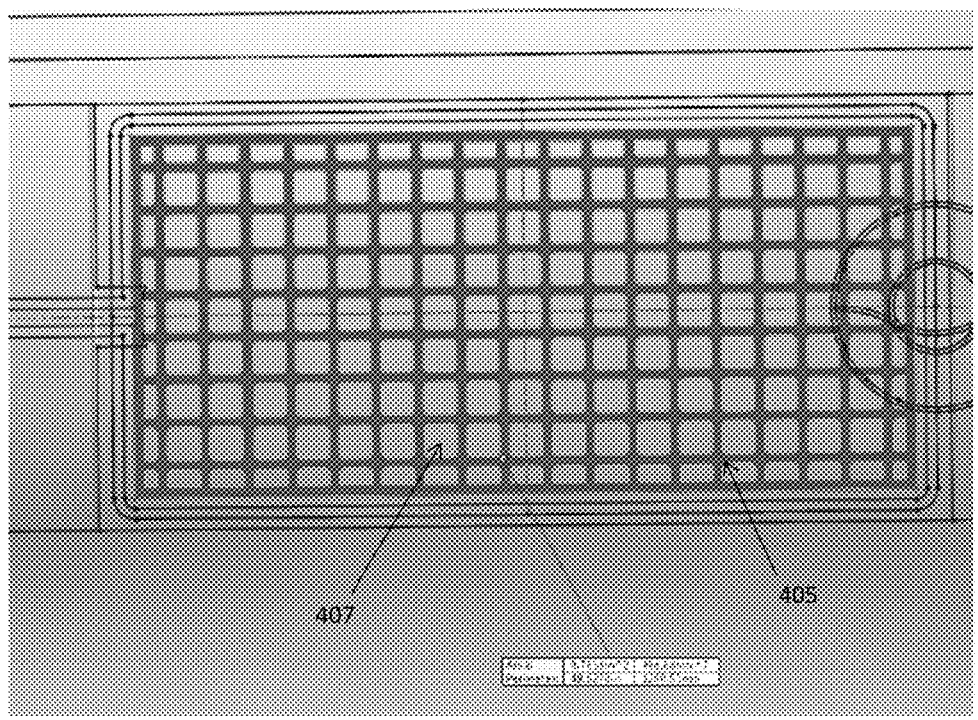

FIGS. 3 and 4 are higher magnification schematic line drawings of the two electrode areas of the electrode apparatus such as that shown in FIG. 1A showing a contiguous Ag layer (filled regions) arranged in a grid 315. It is important that the non-consumptive conductive Ag layer be contiguous (i.e. connected) so that current can flow to all areas of the electrode.

In schematics of FIGS. 1A-1D, 3, and 4, the generally rectangular outlines indicate the position of voids 317 in an electrode (conductive) layer of the active region, although a round area 319 around one electrode connector (snap connector 320) the rectangles are modified to incorporate this rounded shape. These figures also illustrate how smaller exclusions (cut-out regions) may be present at some portions of the electrode area (on the edges in this case, though in some embodiments the density of exclusions is higher toward the center of the electrode). In FIG. 3, the ratio of edges of the electrically conductive layer (e.g., the Ag layer) to the outer perimeter of the active region is greater than 4× (e.g., approximately 6×). In FIG. 4, as in FIG. 3, the electrically conductive layer (first electrically conductive layer, Ag layer 405) is a contiguous grid pattern having a plurality of void regions 407; the ratio of the edges formed by this electrically conductive layer active region is greater than 6× (e.g., approximately 13×).

Figure 10E:
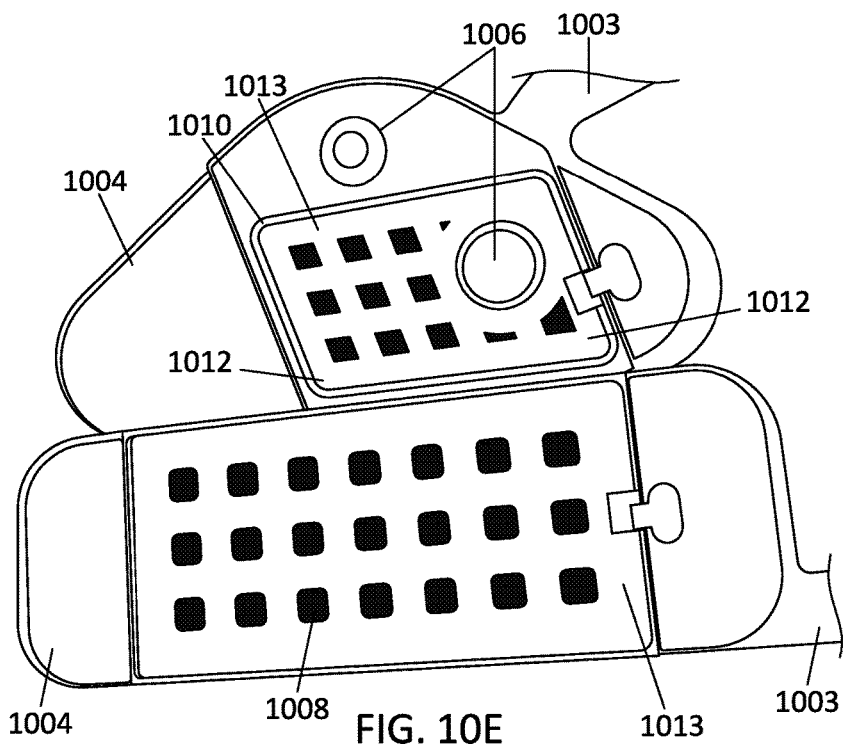
FIG. 10E shows a higher magnification view of one electrode area of a flexible electrode assembly that has a Ag—AgCl layer of a multilayer electrode comprising a 'grid' pattern and indicates regional conversion of AgCl to Ag across the electrode area as indicated by a darkened coloration in some areas of the electrode after use by a subject for transdermal electrical stimulation.

FIG. 10E shows a prototype electrode apparatus having modified grid-style voids to improve the uniformity of current distribution and AgCl→Ag reactions. PET substrate connector regions 1003 conductively connect the two multi-layer electrodes that are surrounded by a dielectric-coating 1004 over which an adhesive is placed for adhering the electrode apparatus (and mechanically and electrically coupled neurostimulator via snaps (behind nylon eyelets 1006)) to the subject. An intermediate conductive carbon layer (black, 1008) can be seen through the voids in the overlying Ag/AgCl layer 1013. After a pulsed, charge imbalanced electrical stimulation waveform is delivered to a subject through this electrode apparatus, the smaller electrode has undergone some discoloration (from AgCl reacting with water in the overlying hydrogel to create darker colored Ag)—though this discoloration is more evenly distributed and less punctuate than that from control electrode (FIG. 10D), the discoloration in FIG. 10E is still concentrated at the edges (particularly the right bottom corner where the trace from the through holes enters the electrode) 1012.

Figure 14:
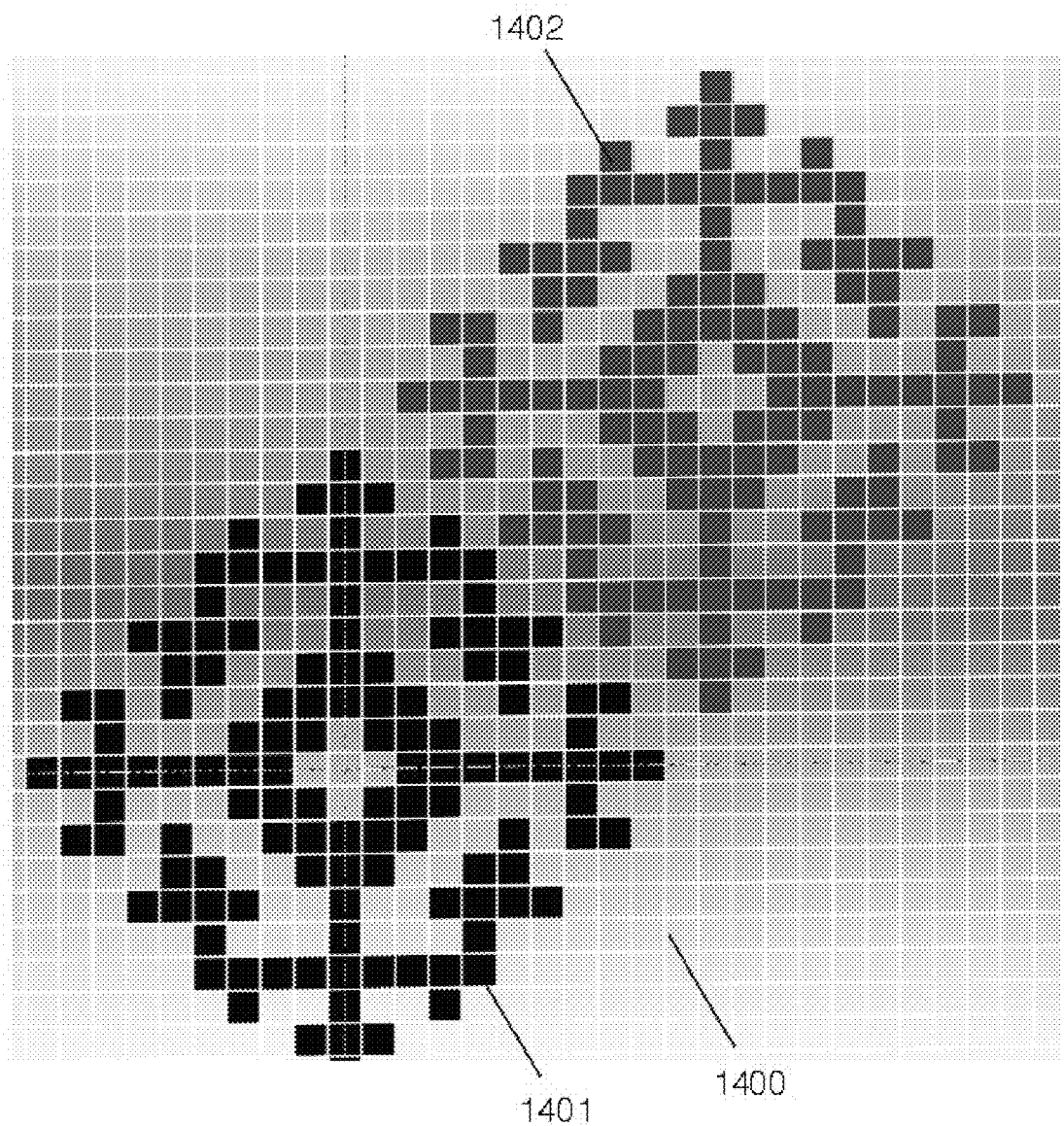
FIG. 14 schematically illustrates a 'snowflake' pattern to create high edge-length contiguous patterns in one layer of a multi-layer electrode.

Example 2: Snowflake-Style Voids to Improve the Uniformity of Current Distribution in Transdermal Electrodes FIG. 14 shows a schematic representation of two iterations 1401, 1402 of a snowflake-style pattern of Ag/AgCl having all active positions (filled squares 1401, 1402) within 1-2 units (voids, 1400) to a neighboring active area. (Note that the snowflake-style pattern in the apparatuses shown in FIGS. 5B-9D and 10A-10C are slightly modified versions of this pattern.) A notable of feature of this design is the non-contiguity of the snowflake-style patterns, thus enabling higher edge length than for a similar pattern that maintained contiguity. The apparent non-contiguity is enabled by an underlying contiguous conductive layer that spans all of the non-contiguous regions (making them all electrically contiguous) and ensures they are isoelectric and form a single electrode. One consideration in this design was to balance the edginess of the design (edge length per unit area) while also having sufficient contiguous and bordered Ag/AgCl areas (as in the center of each of these snowflake-style patterns) so that the electrochemistry could be effectively shared across many grid positions. (In contrast, a design that used a checkerboard pattern would maximize edge length per unit area but do so at the risk of consuming each active single grid region at slightly different rates due to unintended non-uniformities in the manufacturing process.

In the design shown in FIG. 14 the grid distance 0.02 inches was selected because this distance represents the minimum feature that can be resolved with the screen-printing methods used to generate the prototype electrode apparatuses shown in FIGS. 5B-9D and 10A-10C. One skilled in the art of electrode design and manufacturing will recognize that similar patterns with smaller feature sizes could achieve higher density of edges per unit area.

FIGS. 5B-9D show line-style schematics of electrode apparatuses designed using a non-contiguous (but electrically connected) snowflake-style pattern as described above for the (top, not including hydrogel) Ag/AgCl layer. This design achieves significantly improved uniformity of current distribution (even relative to the grid-style voids of example 1), leading to improved comfort and efficiency of stimulation and reduced material cost.

Figure 5A:
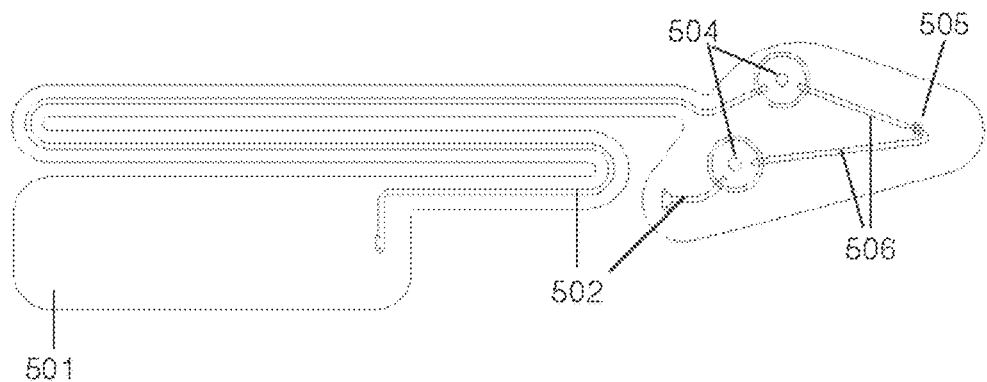
FIG. 5A shows a schematic line drawing of the upper surface of a flexible electrode apparatus configured to connect to a user's temple and neck and including conductive paths and the positioning of conductive snap connectors to a neurostimulator module.

FIG. 5A shows a schematic line drawing of the upper surface of a flexible electrode apparatus configured to connect to a user's temple and neck and including conductive paths on a PET substrate 501 and the positioning of conductive snap connectors through holes 504 to a neurostimulator module (not shown). Connector paths 506 to capacitor 505 (not shown) may be used by the neurostimulator to identify the type of electrode apparatus as described in PCT Patent Application No. PCT/US2015/031424, filed May 18, 2015, titled "WEARABLE TRANSDERMAL NEUROSTIMULATORS", Publication No. WO 2015/183620. Connector paths 502 to conductive through-holes allow electrical communication from the neurostimulator to the electrodes on the lower surface.

Figure 5B:
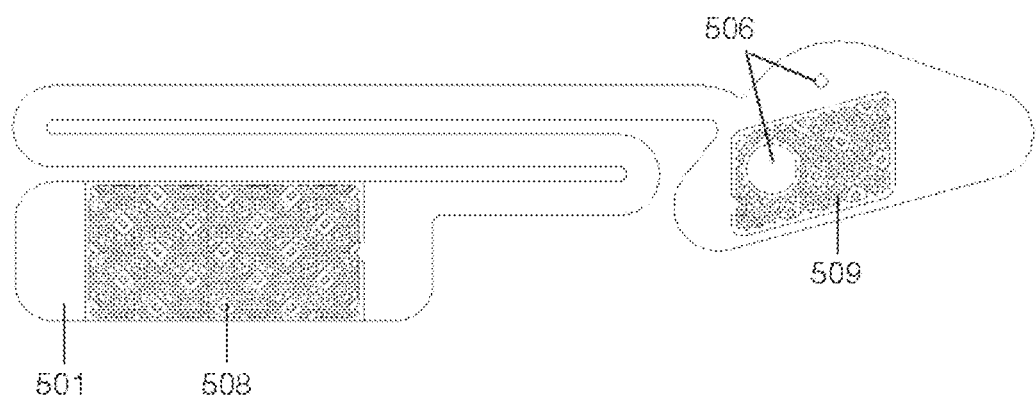
FIG. 5B shows a schematic line drawing of the lower surface of a flexible electrode apparatus configured to connect to a user's temple and neck and including the outline of the Ag—AgCl layer of two multilayer electrodes comprising a 'snowflake' pattern.

FIG. 5B shows a schematic line drawing of the lower surface of a flexible electrode apparatus configured to connect to a user's temple and neck and including the outline of the Ag/AgCl layer of two multilayer electrodes comprising a 'snowflake-style' pattern 508, 509. Positions 506 indicate where snap connectors pass through PET substrate 501 but do not make direct electrical contact with the underlying electrode area 509.

Figure 6A:
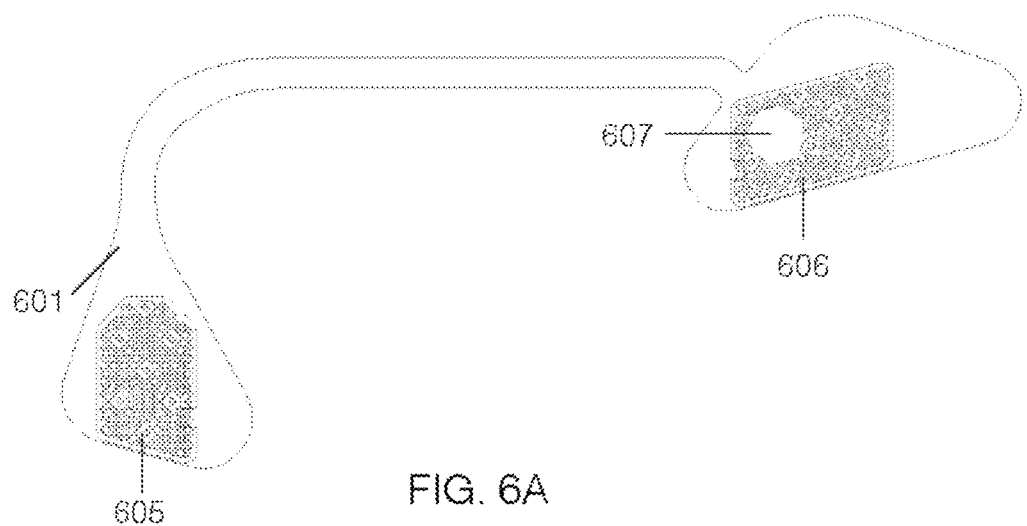
FIG. 6A shows a schematic line drawing of the lower surface of a flexible electrode apparatus configured to connect to a user's temple and mastoid and including the outline of the Ag—AgCl layer of two multilayer electrodes comprising a 'snowflake' pattern.

FIG. 6A shows a schematic line drawing of the lower surface of a flexible electrode apparatus configured to connect to a user's temple and mastoid and including the outline of the Ag—AgCl layer of two multilayer electrodes comprising a 'snowflake-style' pattern 605, 606. The snowflake-style pattern on the triangular (temple-facing) electrode has a round exclusion where a snap connector passes through the PET substrate 601.

Figure 6B:
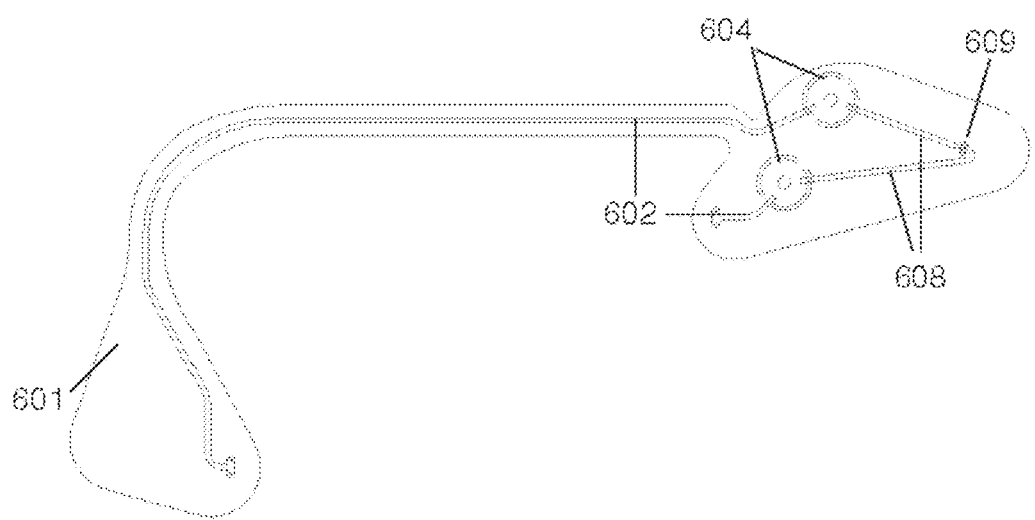
FIG. 6B shows a schematic line drawing of the upper surface of a flexible electrode apparatus configured to connect to a user's temple and neck and including conductive paths and the positioning of conductive snap connectors to a neurostimulator module.

FIG. 6B shows a schematic line drawing of the upper surface of a flexible electrode apparatus configured to connect to a user's temple and neck and including conductive paths and the positioning of conductive snap connectors 604 to a neurostimulator module. Connector paths 608 to capacitor 609 (not shown) may be used by the neurostimulator to identify the type of electrode apparatus as described in PCT/US2015/031424, filed May 18, 2015, titled "WEARABLE TRANSDERMAL NEUROSTIMULATORS", Publication No. WO 2015/183620. Connector paths 602 to conductive through-holes allow electrical communication from the neurostimulator to the electrodes on the lower surface.

FIGS. 7A-9D show higher magnification zooms of the electrode areas of the two exemplar electrode apparatuses shown in FIGS. 5B and 6A. Three of the layers of the active region of the electrodes are shown, including offsets and relative position within the electrode layer stack, similar to that shown in FIG. 11B.

FIGS. 7A-7D show connector region of PET substrate 701; snap connector through hole positioning 703; PET substrate area to position (for example) biocompatible adhesive 702, dielectric boundary 706, 707 around the active region; a first contiguous Ag layer with grid-style voids (first layer of the electrode, relative to the PET substrate) 704; a second, conductive carbon layer 709 (the second layer of the electrode, relative to the PET substrate); and a third layer comprising a (non-contiguous) snowflake-style Ag/AgCl pattern with high edge-length having circuitous voids (third layer of the electrode, relative to the PET substrate) 708.

Figure 7A:
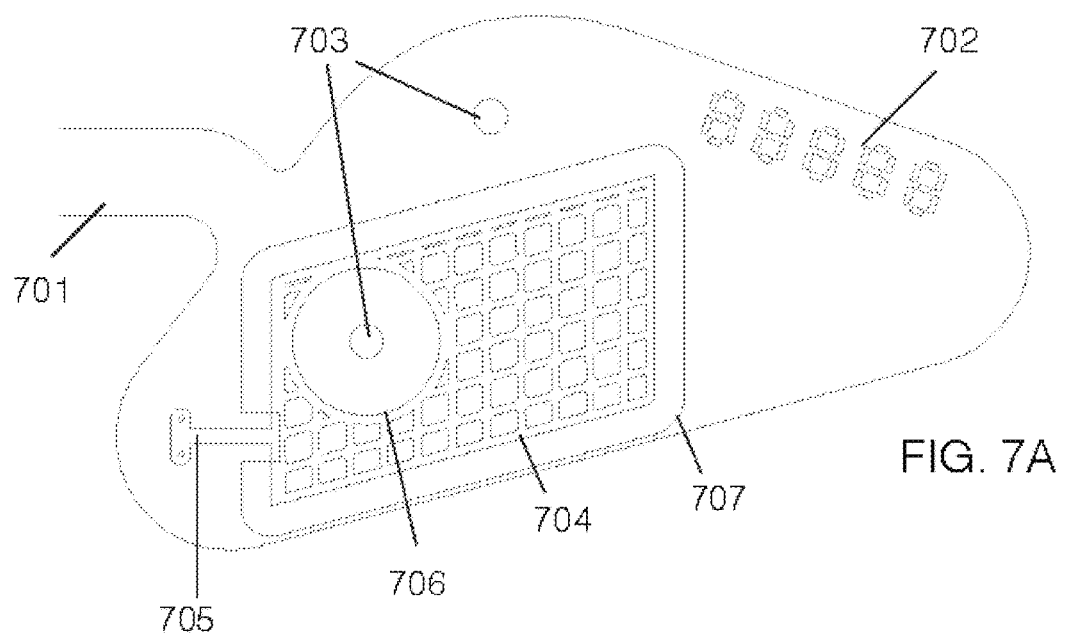
FIG. 7A shows a schematic line drawing of the portion of the lower surface of a flexible electrode apparatus configured to connect to a user's temple and including the outline of one layer of a multilayer electrode comprising a contiguous Ag layer.

FIG. 7A shows a schematic line drawing of the portion of the lower surface of a flexible electrode apparatus configured to connect to a user's temple and including the outline of first electrode layer of a multilayer electrode comprising a contiguous Ag layer 704 that connects by conductive path 705 to conductive vias electrically connecting to the upper surface of the electrode apparatus.

Figure 7B:
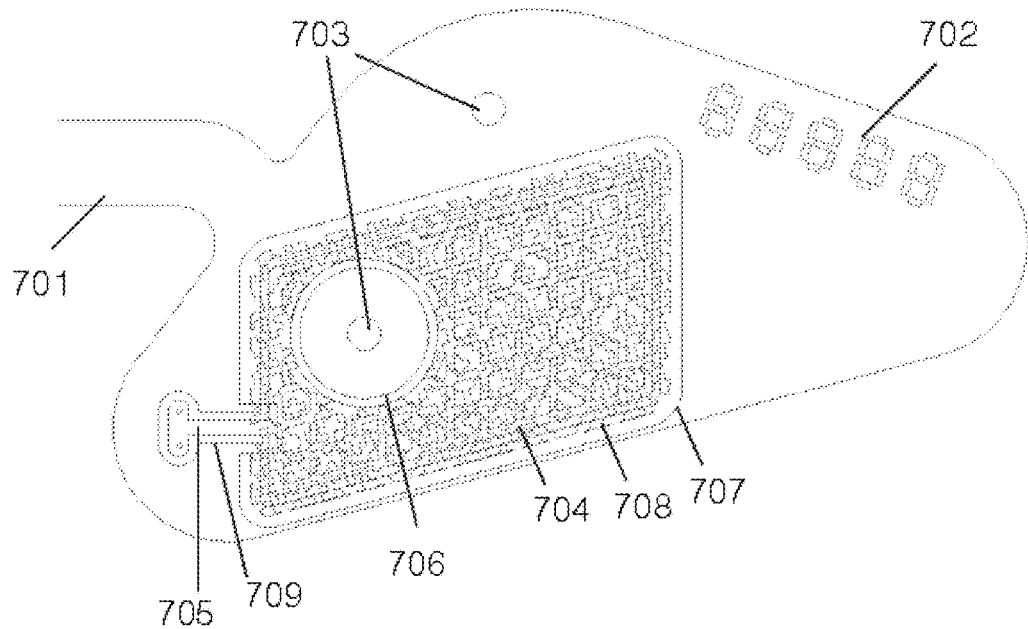
FIG. 7B shows a schematic line drawing of the portion of the lower surface of a flexible electrode apparatus configured to connect to a user's temple and including the outline of all three layers of a multilayer electrode.

FIG. 7B shows a schematic line drawing of a portion of the lower surface of a flexible electrode apparatus configured to connect to a user's temple and including all three layers of a multilayer electrode: a contiguous first conductive layer (e.g., Ag layer), an intermediate mildly insulating (e.g., carbon) layer, and a second conductive layer (e.g., Ag/AgCl layer) stacked sequentially atop each other. Because of the overlap, it is difficult to distinguish the separate three layers in this view.

Figure 7C:
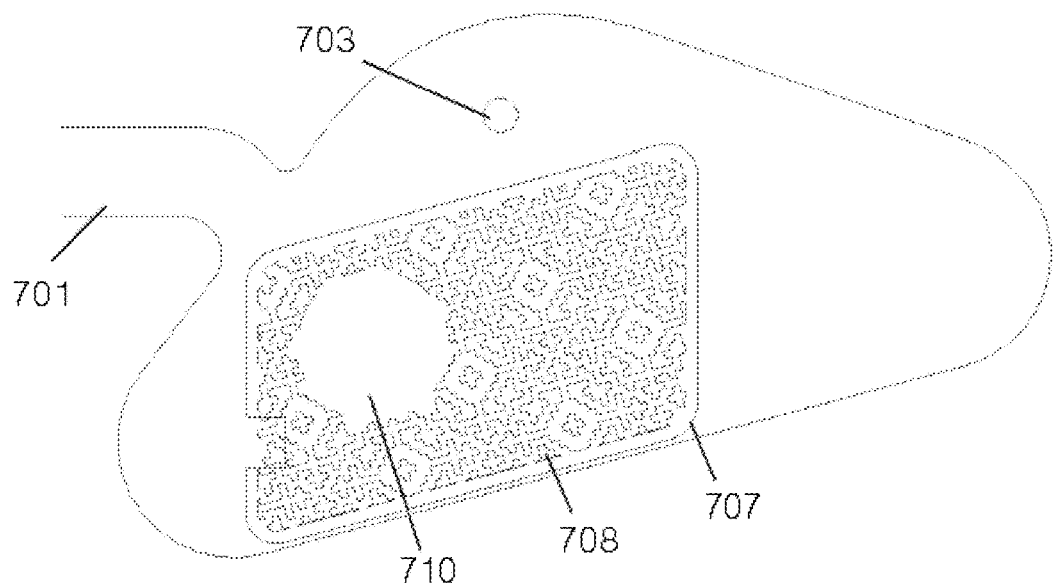
FIG. 7C shows a schematic line drawing of the portion of the lower surface of a flexible electrode apparatus configured to connect to a user's temple and including the outline of the Ag—AgCl layer of a multilayer electrode comprising a 'snowflake' pattern.

FIG. 7C shows a schematic line drawing of the portion of the lower surface of a flexible electrode apparatus configured to connect to a user's temple and showing just the outline of the Ag—AgCl layer of a multilayer electrode comprising a 'snowflake-style' pattern 708 surrounding a snap connector exclusion region 710.

Figure 7D:
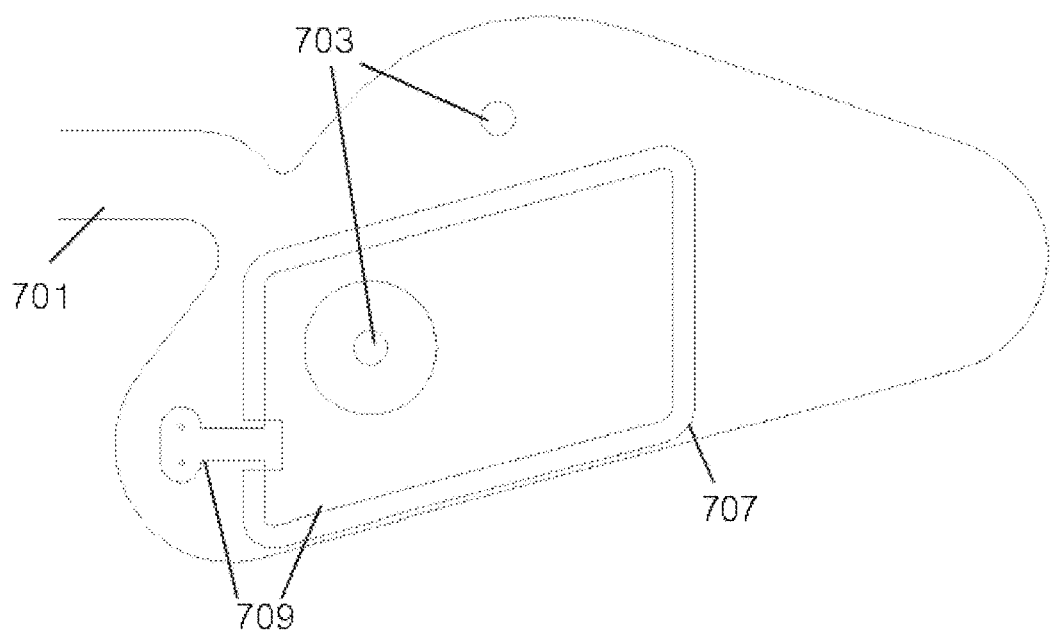
FIG. 7D shows a schematic line drawing of the portion of the lower surface of a flexible electrode apparatus configured to connect to a user's temple and including the outline of the conductive carbon layer of a multilayer electrode.

FIG. 7D shows a schematic line drawing of the portion of the lower surface of a flexible electrode apparatus configured to connect to a user's temple and including the outline of the conductive carbon layer of a multilayer electrode 709.

Figure 8A:
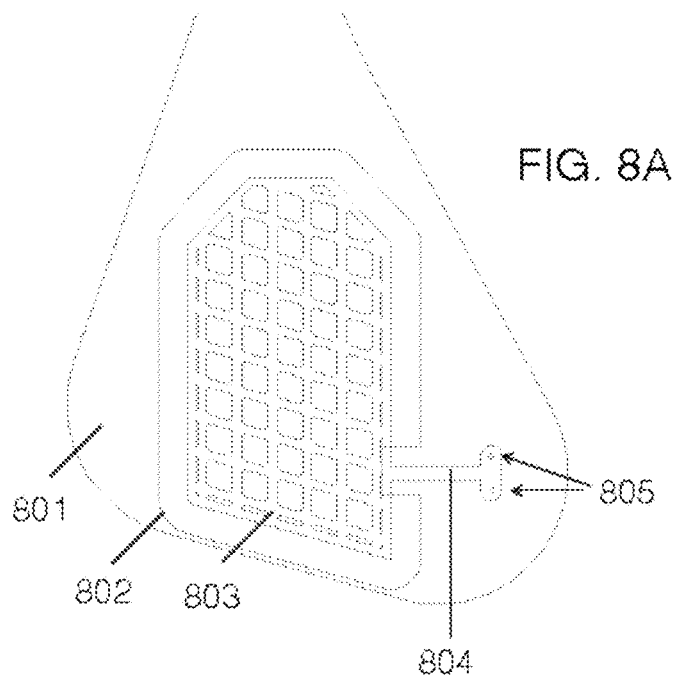
FIG. 8A shows a schematic line drawing of the portion of the lower surface of a flexible electrode apparatus configured to connect to a user's mastoid and including the outline of one layer of a multilayer electrode comprising a contiguous Ag layer.

FIG. 8A shows a schematic line drawing of the portion of the lower surface of a flexible electrode apparatus on a PET substrate 801 configured to connect to a user's mastoid and including the outline of one layer of a multilayer electrode comprising a contiguous Ag layer 803 that connects by conductive path 804 to conductive vias 805 to the upper surface of the electrode apparatus. The PET substrate is covered by an insulating dielectric outside trace 802.

Figure 8B:
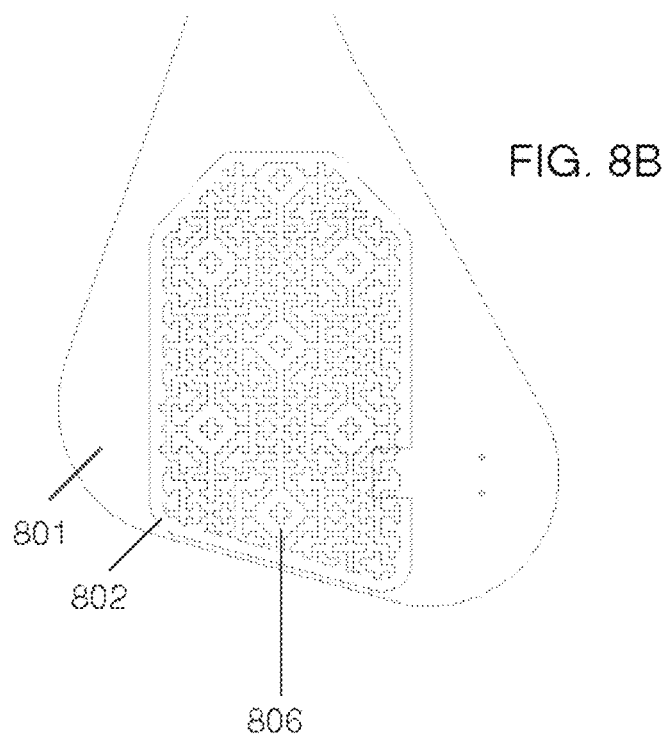
FIG. 8B shows a schematic line drawing of the portion of the lower surface of a flexible electrode apparatus configured to connect to a user's mastoid and including the outline of the Ag—AgCl layer of a multilayer electrode comprising a 'snowflake' pattern.

FIG. 8B shows a schematic line drawing of the portion of the lower surface of a flexible electrode apparatus configured to connect to a user's mastoid and including the outline of the Ag/AgCl layer of a multilayer electrode comprising a 'snowflake-style' pattern 806.

Figure 8C:
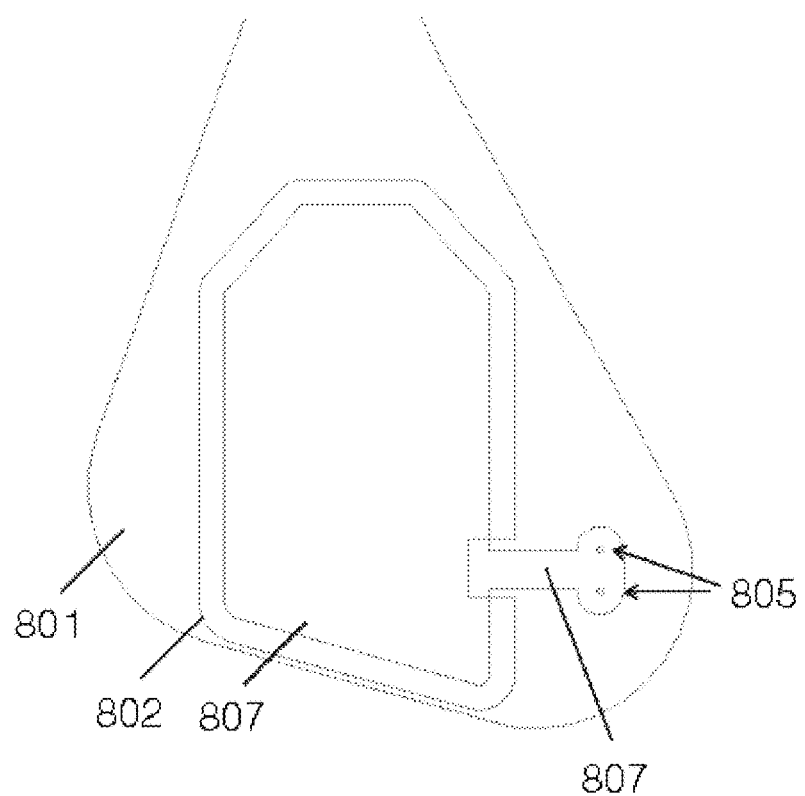
FIG. 8C shows a schematic line drawing of the portion of the lower surface of a flexible electrode apparatus configured to connect to a user's mastoid and including the outline of the conductive carbon layer of a multilayer electrode.

FIG. 8C shows a schematic line drawing of the portion of the lower surface of a flexible electrode apparatus configured to connect to a user's mastoid and including the outline of the conductive carbon layer of a multilayer electrode 807. The three layers shown in FIGS. 8A-8C may be layered atop each other as described above, so that the mildly insulating layer (e.g., carbon layer 807 in FIG. 8C) is sandwiched between the first electrically conductive layer (803 in FIG. 8A) and the second electrically conductive layer (806 in FIG. 8B). The layers may be arranged so that each subsequent layer overlaps or covers the edges of the adjacent layer. The entire stack may be covered by or include a conductive gel (e.g., hydrogel), and may be layered on an appropriate substrate (e.g., PET).

Figure 9A:
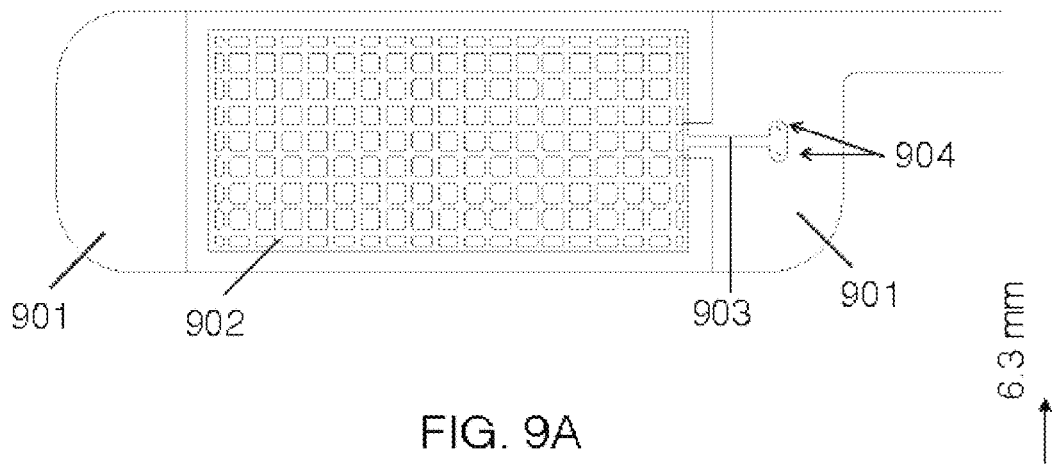
FIG. 9A shows a schematic line drawing of the portion of the lower surface of a flexible electrode apparatus configured to connect to a user's neck and including the outline of one layer of a multilayer electrode comprising a contiguous Ag layer.

FIG. 9A shows a schematic line drawing of the portion of the lower surface of a flexible electrode apparatus on a PET substrate 901 configured to connect to a user's neck and including the outline of one layer of a multilayer electrode comprising a contiguous Ag layer 902 that connects by conductive path 903 to conductive vias 904 that pass to the upper surface of the electrode apparatus.

Figure 9B:
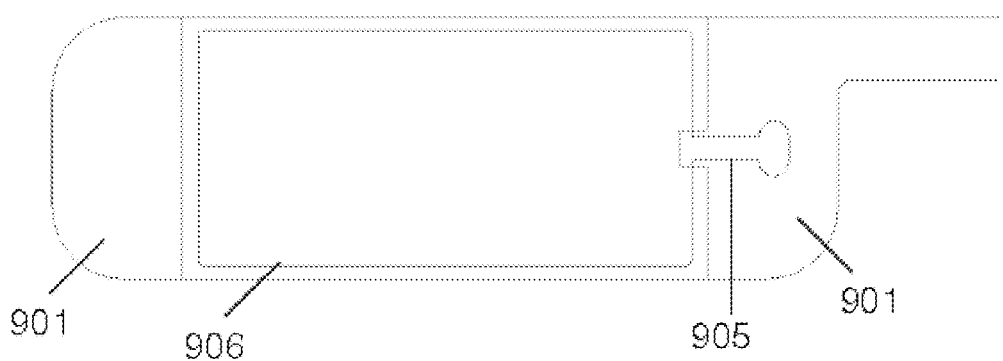
FIG. 9B shows a schematic line drawing of the portion of the lower surface of a flexible electrode apparatus configured to connect to a user's neck and including the outline of the conductive carbon layer of a multilayer electrode.

FIG. 9B shows a schematic line drawing of the portion of the lower surface of a flexible electrode apparatus configured to connect to a user's neck and including the outline of the conductive carbon layer of a multilayer electrode 905, 906.

Figure 9C:
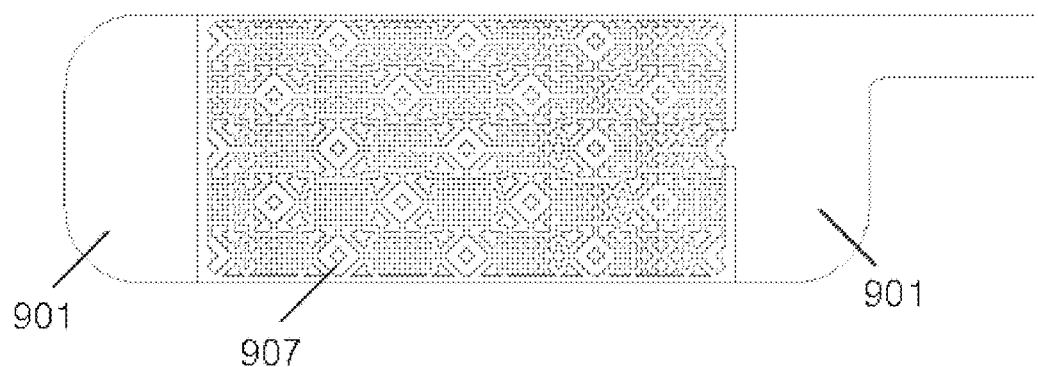
FIG. 9C shows a schematic line drawing of the portion of the lower surface of a flexible electrode apparatus configured to connect to a user's neck and including the outline of the Ag—AgCl layer of a multilayer electrode comprising a 'snowflake' pattern.

FIG. 9C shows a schematic line drawing of the portion of the lower surface of a flexible electrode apparatus configured to connect to a user's neck and including the outline of the Ag—AgCl layer of a multilayer electrode comprising a 'snowflake-style' pattern 907.

Figure 9D:
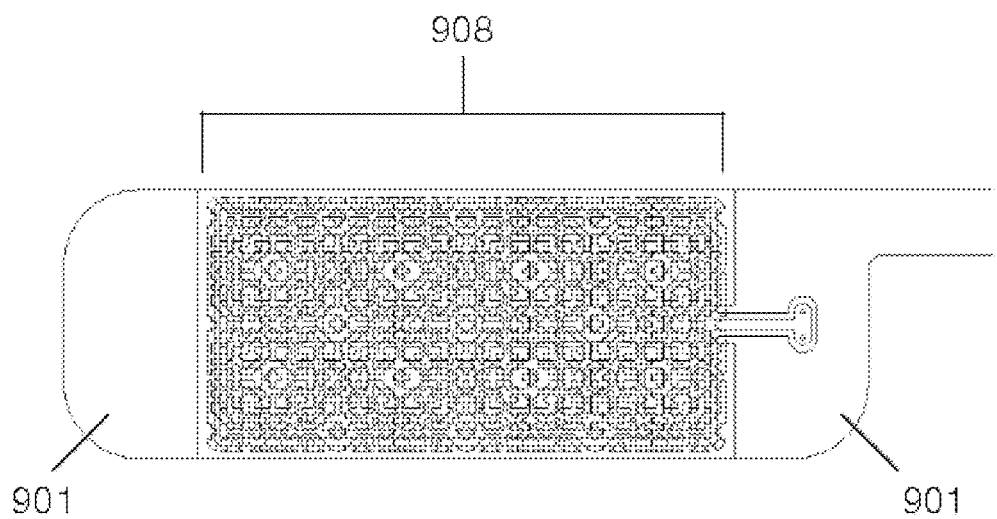
FIG. 9D shows a schematic line drawing of the portion of the lower surface of a flexible electrode apparatus configured to connect to a user's neck and including the outline of all three layers of a multilayer electrode.

FIG. 9D shows a schematic line drawing of the portion of the lower surface of a flexible electrode apparatus configured to connect to a user's neck and including the outline of all three layers of a multilayer electrode 908 (in the active region of the electrode).

FIGS. 10A-10C show prototypes of the designs shown in FIGS. 5A-9D. For example, FIG. 10A is a picture of the lower (patient-facing) side of an unused transdermal electrode configured to stimulate the temple and mastoid regions through an attachable neurostimulator (not shown). Both temple electrode 1005 and mastoid electrode 1001 have overlying hydrogel and a snowflake-style pattern of the Ag—AgCl layer so that the black conductive carbon layer underneath can be seen through the Ag/AgCl layer. Regions of the PET substrate next to the electrodes have a biocompatible adhesive 1004, 1002 for helping affix the electrode apparatus to the subject's skin.

FIGS. 10B and 10C are higher magnification pictures of the temple electrode area of a transdermal electrode before (FIG. 10B) and after (FIG. 10C) use by a subject. The figures show connector region 1003, nylon eyelets of snap connectors 1006, PET substrate region with overlying biocompatible adhesive 1004, PET region uncoated with dielectric 1010, conductive via region 1009, snowflake-style Ag—AgCl layer 1007, and underlying conductive carbon layer (black, 1008) viewable through the voids of the Ag—AgCl layer. After use the Ag—AgCl layer is significantly darker, reflecting the uniform transformation of light AgCl to dark Ag. The uniformity of the discoloration indicates the uniformity of both charge distribution and electrochemistry. Subjects who receive transdermal electrical stimulation with electrodes having voids (i.e. the snowflake-style Ag—AgCl layer) report more comfortable and effective stimulation.

Example 3: Implanted Electrodes with Voids

In other exemplary embodiments of the invention, an electrode having exclusions or voids in one or more layer may be configured for implantation in order to deliver current more uniformly, comfortably, and/or efficiently targeting neural tissue or another portion of the body with current delivered by a stimulator unit conductively coupled to the electrode apparatus. In general, implantable electrodes with voids in one or more layer may use a multilayer electrode design. One advantage of having a multi-layer design is that the outermost layer (closest to biological target tissue of electrical stimulation) may contain non-contiguous patterns that are still shorted (isopolar) via underlying conductive layers that extend beyond the non-contiguous edges of patterns having voids. This design permits a larger edge-length per unit area (for a given feature size) relative to single layer electrodes that generally require a contiguous design to maintain isoelectric potentials.

Note that the scale for FIGS. 1A-1D, 5A-5B, 6A-6B, 7A-7D, and 10A-10E may be estimated by the center-to-center distance of the two connector snaps (and aligned through-holes, nylon covers, etc.) which is approximately 19 mm in these examples; other dimensions may be used. The electrode regions shown in FIGS. 8A-8C and 9A-9D, though lacking a snap connector region may be the same size as those regions shown with the full electrode assemblies in FIGS. 5B and 6A.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An electrode for transdermal electrical stimulation, the electrode comprising:
  a substrate; and
  a multi-layered active region comprising:
    a first layer on the substrate that is electrically contiguous and conductive and is arranged in a pattern forming a plurality of one or more combinations of branches and voids, wherein the pattern extends through a width of the first layer, a second layer on the first layer, a third layer that is electrically contiguous and conductive on the second layer, wherein the second layer is sandwiched between the first and third layers and has a resistivity that is greater than 5× the resistivity of the first or third layers;

wherein a ratio of edges formed by the pattern of the first layer to a perimeter of the multi-layered active region is greater than 4.

2. The electrode of claim 1, wherein the substrate is planar.

3. The electrode of claim 1, wherein the substrate is Polyethylene Terephthalate (PET).

4. The electrode of claim 1, further comprising a conductive via between the first layer and an electrical connector configured to connect the electrode to an electrical stimulator.

5. The electrode of claim 4, wherein the electrical connector comprises a snap connector.

6. The electrode of claim 1, further comprising a second multi-layered active region on the substrate.

7. The electrode of claim 1, wherein the first layer is arranged in a grid pattern.

8. The electrode of claim 1, wherein the first layer is arranged in a snowflake pattern.

9. The electrode of claim 1, wherein the first layer comprises a layer of silver (Ag).

10. The electrode of claim 1, wherein the second layer comprises a conductive carbon layer.

11. The electrode of claim 1, wherein the second layer has a resistance that is greater than 10× a resistance of the first layer or the third layer.

12. The electrode of claim 1, wherein the third layer comprises Ag/AgCl.

13. The electrode of claim 1, wherein the third layer overlaps the second layer and wherein the second layer overlaps the third layer.

14. The electrode of claim 1, wherein the ratio of edges formed by the pattern of the first layer to the perimeter of the multi-layered active region is greater than 10.

15. The electrode of claim 1, wherein the ratio of edges formed by the pattern of the first layer to the perimeter of the multi-layered active region is greater than 15.

16. The electrode of claim 1, further comprising a hydrogel covering the third layer.

17. The electrode of claim 1, wherein the third layer is arranged in a pattern forming a plurality of one or more combinations of branches and voids, wherein the pattern extends through a width of the third layer.

18. An electrode for transdermal electrical stimulation, the electrode comprising:

a planar substrate; and a multi-layered active region comprising:

a first layer on the substrate that is electrically contiguous and conductive and is arranged in a contiguous pattern forming a plurality of one or more combinations of branches and voids, wherein the pattern extends through a width of the first layer, a second layer on the first layer, a third layer that is electrically contiguous and conductive on the second layer, and a hydrogel covering the third layer, wherein the second layer is sandwiched between the first and third layers and has a resistivity that is greater than 10× the resistivity of the first or third layers;

wherein a ratio of edges formed by the first layer to a perimeter of the multi-layered active region is greater than 4.

19. An electrode for transdermal electrical stimulation, the electrode comprising:

a planar substrate; and a multi-layered active region comprising:

a first layer on the substrate comprising an electrically contiguous and conductive Ag layer that is arranged in a contiguous pattern forming a plurality of one or more combination of branches and voids, wherein the pattern extends through a width of the first layer, a second layer comprising a conductive carbon layer on the first layer, a third layer comprising a contiguous Ag/AgCl conductive layer on the second layer, and a hydrogel covering the third layer, wherein the second layer is sandwiched between the first and third layers and has a resistivity that is greater than 10× the resistivity of the first or third layers;

wherein a ratio of edges formed by the first layer to a perimeter of the multi-layered active region is greater than 4.

* * * * *